(12) United States Patent
Grunenberg et al.

(10) Patent No.: US 8,492,385 B2
(45) Date of Patent: Jul. 23, 2013

(54) CRYSTALLINE MODIFICATIONS OF N-ALPHA-(2,4,6-TRIISOPROPYLPHENYLSULFONYL)-3-HYDROXYAMIDINO-(L)- PHENYLALANINE 4-ETHOXYCARBONYLPIPERAZIDE AND/OR SALTS THEREOF

(75) Inventors: Alfons Grunenberg, Dormagen (DE); Jana Lenz, Leinfelden-Echterdingen (DE)

(73) Assignee: Wilex AG, Munich (DE)

( * ) Notice: Subject to any disclaimer, the term of this patent is extended or adjusted under 35 U.S.C. 154(b) by 476 days.

(21) Appl. No.: 12/749,140

(22) Filed: Mar. 29, 2010

(65) Prior Publication Data

US 2010/0266679 A1 Oct. 21, 2010

Related U.S. Application Data

(62) Division of application No. 11/664,266, filed as application No. PCT/EP2005/012589 on Nov. 24, 2005, now Pat. No. 7,713,980.

(30) Foreign Application Priority Data

Nov. 26, 2004 (DE) .......................... 10 2004 057 195

(51) Int. Cl.
*A61K 31/4965* (2006.01)
*C07D 295/00* (2006.01)

(52) U.S. Cl.
USPC .................................................. 514/255.01

(58) Field of Classification Search
USPC .................................................. 514/255.01
See application file for complete search history.

(56) References Cited

U.S. PATENT DOCUMENTS

| 2004/0110831 A1 | 6/2004 | Ziegler |
| 2005/0245757 A1 | 11/2005 | Wosikowski-Buters et al. |

FOREIGN PATENT DOCUMENTS

| WO | 02/074756 A2 | 9/2002 |
| WO | 03/072559 A1 | 9/2003 |
| WO | WO 03/072559 A | 9/2003 |
| WO | WO 2004/011449 | 2/2004 |
| WO | WO 2004/011449 A | 2/2004 |
| WO | WO 2004/067522 A | 8/2004 |
| WO | WO 2004/103984 | 12/2004 |
| WO | WO 2004/103984 A | 12/2004 |
| WO | WO 2006/032461 | 3/2006 |

OTHER PUBLICATIONS

De Vries, et al., Components of the Plasminogen Activation System in Uveal Melanoma—A Clinico-pathological Study, J. of Pathology, vol. 175: 59-67 (1995).*
Bastin et al., Organic Process Research & Development, vol. 4, pp. 427-435 (2000).

* cited by examiner

*Primary Examiner* — Erich A Leeser
(74) *Attorney, Agent, or Firm* — Gianna Julian-Arnold; Saul Ewing LLP

(57) ABSTRACT

The present invention relates to novel crystalline modifications of N-α-(2,4,6-triisopropylphenyl-sulfonyl)-3-hydroxyamidino-(L)-phenylalanine 4-ethoxy-carbonylpiperazide and/or salts thereof, which can be used as pharmaceutical agents, and to pharmaceutical compositions and pharmaceutical uses comprising these novel crystalline modifications.

9 Claims, 28 Drawing Sheets

List of the 9 highest peaks

Crystal data and structure refinement for WX-671.2

| | |
|---|---|
| Empirical formula | C64 H98 N10 O19 S3 |
| Formula weight | 1407.70 |
| Temperature | 90(2) K |
| Wavelength | 1.54178 Å |
| Crystal system | Orthorhombic |
| Space group | $P2_12_12$ |
| Unit cell dimensions | a = 14.296(2) Å   α = 90°. |
| | b = 47.363(8) Å   β = 90°. |
| | c = 10.5782(17) Å   γ = 90°. |
| Volume | 7163(2) Å$^3$ |
| Z | 4 |
| Density (calculated) | 1.305 Mg/m$^3$ |
| Absorption coefficient | 1.577 mm$^{-1}$ |
| F(000) | 3008 |
| Crystal size | 0.06 × 0.05 × 0.015 mm$^3$ |
| Theta range for data collection | 1.87 to 71.54°. |
| Index ranges | −17 ≤ h ≤ 17, −56 ≤ k ≤ 57, |
| | −11 ≤ l ≤ 10 |
| Collected reflections | 47 840 |
| Independent reflections | 12 632 [R(int) = 0.1231] |
| Completeness at theta = 71.54° | 91.1% |
| Absorption correction | SADABS (Bruker AXS) |
| Refinement methods | Full-matrix least-squares on F$^2$ |
| Data/restrictions/parameters | 12 632/0/891 |
| Matching test for F$^2$ | 1.013 |
| Final R indices [I>2sigma(I)] | R1 = 0.0801, wR2 = 0.1705 |
| R indices (all data) | R1 = 0.1429, wR2 = 0.2016 |
| Absolute structure parameters | 0.03(3) |
| Extinction coefficient | 0.00027(4) |
| Greatest diff. peak and valley | 0.392 and −0.355 e.Å$^{-3}$ |

Figure 8

Bond lengths [Å] and angles [°] for WX-671.2

| | |
|---|---|
| S(1A)-O(5A) | 1.424(4) |
| S(1A)-O(6A) | 1.433(4) |
| S(1A)-N(5A) | 1.637(6) |
| S(1A)-C(18A) | 1.783(6) |
| C(1A)-C(2A) | 1.377(10) |
| C(1A)-C(6A) | 1.389(10) |
| C(1A)-C(8A) | 1.490(9) |
| N(1A)-C(7A) | 1.315(10) |
| N(1A)-O(1A') | 1.68(9) |
| O(1A)-N(2A) | 1.394(9) |
| N(2A)-C(7A) | 1.302(10) |
| C(2A)-C(3A) | 1.401(10) |
| O(2A)-C(10A) | 1.224(8) |
| N(3A)-C(10A) | 1.348(8) |
| N(3A)-C(11A) | 1.447(8) |
| N(3A)-C(14A) | 1.476(9) |
| C(3A)-C(4A) | 1.418(10) |
| C(3A)-C(7A) | 1.464(12) |
| O(3A)-C(15A) | 1.238(10) |
| C(4A)-C(5A) | 1.379(11) |
| N(4A)-C(15A) | 1.355(10) |
| N(4A)-C(13A) | 1.455(9) |
| N(4A)-C(12A) | 1.470(9) |
| O(4A)-C(15A) | 1.297(10) |
| O(4A)-C(16A) | 1.487(10) |
| N(5A)-C(9A) | 1.437(8) |
| C(5A)-C(6A) | 1.397(10) |
| C(8A)-C(9A) | 1.551(9) |
| C(9A)-C(10A) | 1.528(9) |
| C(11A)-C(12A) | 1.526(9) |
| C(13A)-C(14A) | 1.496(10) |
| C(16A)-C(17A) | 1.346(12) |
| C(18A)-C(19A) | 1.420(8) |
| C(18A)-C(23A) | 1.428(9) |
| C(19A)-C(20A) | 1.395(9) |

Figure 8 (continued)

| | |
|---|---|
| C(19A)-C(24A) | 1.514(9) |
| C(20A)-C(21A) | 1.383(9) |
| C(21A)-C(22A) | 1.369(9) |
| C(21A)-C(27A) | 1.517(9) |
| C(22A)-C(23A) | 1.397(9) |
| C(23A)-C(30A) | 1.510(9) |
| C(24A)-C(26A) | 1.533(9) |
| C(24A)-C(25A) | 1.543(9) |
| C(27A)-C(28A) | 1.531(9) |
| C(27A)-C(29A) | 1.538(9) |
| C(30A)-C(32A) | 1.518(9) |
| C(30A)-C(31A) | 1.522(9) |
| S(1L)-O(3L) | 1.468(6) |
| S(1L)-O(1L) | 1.471(5) |
| S(1L)-O(2L) | 1.479(5) |
| S(1L)-O(4L) | 1.498(5) |
| N(1B)-C(7B) | 1.318(9) |
| C(1B)-C(2B) | 1.382(10) |
| C(1B)-C(6B) | 1.406(10) |
| C(1B)-C(8B) | 1.486(10) |
| O(1B)-N(2B) | 1.389(8) |
| S(1B)-O(5B) | 1.420(5) |
| S(1B)-O(6B) | 1.433(5) |
| S(1B)-N(5B) | 1.651(5) |
| S(1B)-C(18B) | 1.790(6) |
| N(2B)-C(7B) | 1.340(10) |
| O(2B)-C(10B) | 1.226(8) |
| C(2B)-C(3B) | 1.400(10) |
| N(3B)-C(10B) | 1.356(8) |
| N(3B)-C(14B) | 1.455(9) |
| N(3B)-C(11B) | 1.462(8) |
| O(3B)-C(15B) | 1.222(9) |
| C(3B)-C(4B) | 1.379(10) |
| C(3B)-C(7B) | 1.474(11) |
| O(4B)-C(15B) | 1.328(8) |
| O(4B)-C(16B) | 1.470(8) |
| N(4B)-C(15B) | 1.368(9) |

Figure 8 (continued)

| | |
|---|---|
| N(4B)-C(13B) | 1.459(8) |
| N(4B)-C(12B) | 1.466(9) |
| C(4B)-C(5B) | 1.408(11) |
| N(5B)-C(9B) | 1.455(8) |
| C(5B)-C(6B) | 1.374(11) |
| C(8B)-C(9B) | 1.555(9) |
| C(9B)-C(10B) | 1.522(9) |
| C(11B)-C(12B) | 1.515(9) |
| C(13B)-C(14B) | 1.516(10) |
| C(16B)-C(17B) | 1.506(10) |
| C(18B)-C(23B) | 1.412(9) |
| C(18B)-C(19B) | 1.419(9) |
| C(19B)-C(20B) | 1.380(9) |
| C(19B)-C(24B) | 1.522(9) |
| C(20B)-C(21B) | 1.394(9) |
| C(21B)-C(22B) | 1.374(9) |
| C(21B)-C(27B) | 1.514(9) |
| C(22B)-C(23B) | 1.390(9) |
| C(23B)-C(30B) | 1.509(9) |
| C(24B)-C(25B) | 1.532(9) |
| C(24B)-C(26B) | 1.538(9) |
| C(27B)-C(28B) | 1.519(9) |
| C(27B)-C(29B) | 1.524(9) |
| C(30B)-C(31B) | 1.527(9) |
| C(30B)-C(32B) | 1.541(9) |
| O(2W)-O(4W) | 1.45(5) |
| O(5A)-S(1A)-O(6A) | 118.8(3) |
| O(5A)-S(1A)-N(5A) | 106.7(3) |
| O(6A)-S(1A)-N(5A) | 105.6(3) |
| O(5A)-S(1A)-C(18A) | 109.5(3) |
| O(6A)-S(1A)-C(18A) | 108.4(3) |
| N(5A)-S(1A)-C(18A) | 107.3(3) |
| C(2A)-C(1A)-C(6A) | 119.0(7) |
| C(2A)-C(1A)-C(8A) | 118.9(7) |
| C(6A)-C(1A)-C(8A) | 122.1(7) |
| C(7A)-N(1A)-O(1A') | 122(3) |
| C(7A)-N(2A)-O(1A) | 116.4(7) |

Figure 8 (continued)

| | |
|---|---|
| C(1A)-C(2A)-C(3A) | 122.4(8) |
| C(10A)-N(3A)-C(11A) | 120.8(6) |
| C(10A)-N(3A)-C(14A) | 126.3(6) |
| C(11A)-N(3A)-C(14A) | 112.5(5) |
| C(2A)-C(3A)-C(4A) | 117.9(7) |
| C(2A)-C(3A)-C(7A) | 120.7(7) |
| C(4A)-C(3A)-C(7A) | 121.3(7) |
| C(5A)-C(4A)-C(3A) | 119.6(7) |
| C(15A)-N(4A)-C(13A) | 118.0(7) |
| C(15A)-N(4A)-C(12A) | 122.6(7) |
| C(13A)-N(4A)-C(12A) | 115.9(6) |
| C(15A)-O(4A)-C(16A) | 116.0(8) |
| C(9A)-N(5A)-S(1A) | 121.0(5) |
| C(4A)-C(5A)-C(6A) | 121.0(7) |
| C(1A)-C(6A)-C(5A) | 120.1(7) |
| N(2A)-C(7A)-N(1A) | 121.9(8) |
| N(2A)-C(7A)-C(3A) | 118.9(8) |
| N(1A)-C(7A)-C(3A) | 119.2(8) |
| C(1A)-C(8A)-C(9A) | 112.9(5) |
| N(5A)-C(9A)-C(10A) | 109.9(5) |
| N(5A)-C(9A)-C(8A) | 109.3(5) |
| C(10A)-C(9A)-C(8A) | 108.3(5) |
| O(2A)-C(10A)-N(3A) | 120.3(7) |
| O(2A)-C(10A)-C(9A) | 119.7(6) |
| N(3A)-C(10A)-C(9A) | 120.0(6) |
| N(3A)-C(11A)-C(12A) | 110.5(6) |
| N(4A)-C(12A)-C(11A) | 108.6(6) |
| N(4A)-C(13A)-C(14A) | 110.2(6) |
| N(3A)-C(14A)-C(13A) | 110.2(6) |
| O(3A)-C(15A)-O(4A) | 123.1(8) |
| O(3A)-C(15A)-N(4A) | 123.6(8) |
| O(4A)-C(15A)-N(4A) | 113.3(8) |
| C(17A)-C(16A)-O(4A) | 108.8(8) |
| C(19A)-C(18A)-C(23A) | 119.5(5) |
| C(19A)-C(18A)-S(1A) | 122.1(5) |
| C(23A)-C(18A)-S(1A) | 118.4(5) |
| C(20A)-C(19A)-C(18A) | 117.7(6) |

Figure 8 (continued)

| | |
|---|---|
| C(20A)-C(19A)-C(24A) | 116.2(6) |
| C(18A)-C(19A)-C(24A) | 126.1(6) |
| C(21A)-C(20A)-C(19A) | 123.7(6) |
| C(22A)-C(21A)-C(20A) | 117.3(6) |
| C(22A)-C(21A)-C(27A) | 121.5(6) |
| C(20A)-C(21A)-C(27A) | 121.1(6) |
| C(21A)-C(22A)-C(23A) | 123.3(6) |
| C(22A)-C(23A)-C(18A) | 118.2(6) |
| C(22A)-C(23A)-C(30A) | 116.5(6) |
| C(18A)-C(23A)-C(30A) | 125.3(6) |
| C(19A)-C(24A)-C(26A) | 112.9(5) |
| C(19A)-C(24A)-C(25A) | 109.7(5) |
| C(26A)-C(24A)-C(25A) | 109.0(5) |
| C(21A)-C(27A)-C(28A) | 110.2(5) |
| C(21A)-C(27A)-C(29A) | 111.8(5) |
| C(28A)-C(27A)-C(29A) | 109.6(6) |
| C(23A)-C(30A)-C(32A) | 109.1(6) |
| C(23A)-C(30A)-C(31A) | 113.2(5) |
| C(32A)-C(30A)-C(31A) | 109.8(5) |
| O(3L)-S(1L)-O(1L) | 110.3(3) |
| O(3L)-S(1L)-O(2L) | 110.8(3) |
| O(1L)-S(1L)-O(2L) | 108.5(3) |
| O(3L)-S(1L)-O(4L) | 109.7(3) |
| O(1L)-S(1L)-O(4L) | 108.6(3) |
| O(2L)-S(1L)-O(4L) | 108.9(3) |
| C(2B)-C(1B)-C(6B) | 117.0(8) |
| C(2B)-C(1B)-C(8B) | 120.8(7) |
| C(6B)-C(1B)-C(8B) | 122.2(7) |
| O(5B)-S(1B)-O(6B) | 118.1(3) |
| O(5B)-S(1B)-N(5B) | 106.4(3) |
| O(6B)-S(1B)-N(5B) | 105.8(3) |
| O(5B)-S(1B)-C(18B) | 109.9(3) |
| O(6B)-S(1B)-C(18B) | 108.2(3) |
| N(5B)-S(1B)-C(18B) | 107.9(3) |
| C(7B)-N(2B)-O(1B) | 117.8(6) |
| C(1B)-C(2B)-C(3B) | 122.5(7) |
| C(10B)-N(3B)-C(14B) | 125.6(6) |

Figure 8 (continued)

| | |
|---|---|
| C(10B)-N(3B)-C(11B) | 120.1(6) |
| C(14B)-N(3B)-C(11B) | 114.0(5) |
| C(4B)-C(3B)-C(2B) | 119.2(8) |
| C(4B)-C(3B)-C(7B) | 121.1(8) |
| C(2B)-C(3B)-C(7B) | 119.6(7) |
| C(15B)-O(4B)-C(16B) | 113.9(5) |
| C(15B)-N(4B)-C(13B) | 119.2(6) |
| C(15B)-N(4B)-C(12B) | 125.1(6) |
| C(13B)-N(4B)-C(12B) | 115.5(6) |
| C(3B)-C(4B)-C(5B) | 119.3(8) |
| C(9B)-N(5B)-S(1B) | 118.2(4) |
| C(6B)-C(5B)-C(4B) | 120.1(7) |
| C(5B)-C(6B)-C(1B) | 121.6(8) |
| N(1B)-C(7B)-N(2B) | 120.9(8) |
| N(1B)-C(7B)-C(3B) | 123.1(8) |
| N(2B)-C(7B)-C(3B) | 116.1(7) |
| C(1B)-C(8B)-C(9B) | 115.3(6) |
| N(5B)-C(9B)-C(10B) | 108.5(5) |
| N(5B)-C(9B)-C(8B) | 108.9(5) |
| C(10B)-C(9B)-C(8B) | 108.1(5) |
| O(2B)-C(10B)-N(3B) | 121.0(7) |
| O(2B)-C(10B)-C(9B) | 119.2(6) |
| N(3B)-C(10B)-C(9B) | 119.6(6) |
| N(3B)-C(11B)-C(12B) | 110.0(5) |
| N(4B)-C(12B)-C(11B) | 109.5(6) |
| N(4B)-C(13B)-C(14B) | 109.8(6) |
| N(3B)-C(14B)-C(13B) | 110.2(6) |
| O(3B)-C(15B)-O(4B) | 125.5(7) |
| O(3B)-C(15B)-N(4B) | 123.2(7) |
| O(4B)-C(15B)-N(4B) | 111.2(6) |
| O(4B)-C(16B)-C(17B) | 105.8(6) |
| C(23B)-C(18B)-C(19B) | 120.4(5) |
| C(23B)-C(18B)-S(1B) | 117.4(5) |
| C(19B)-C(18B)-S(1B) | 122.2(5) |
| C(20B)-C(19B)-C(18B) | 118.0(6) |
| C(20B)-C(19B)-C(24B) | 116.3(6) |
| C(18B)-C(19B)-C(24B) | 125.7(6) |

Figure 8 (continued)

| | |
|---|---|
| C(19B)-C(20B)-C(21B) | 123.3(6) |
| C(22B)-C(21B)-C(20B) | 116.4(6) |
| C(22B)-C(21B)-C(27B) | 122.1(6) |
| C(20B)-C(21B)-C(27B) | 121.3(6) |
| C(21B)-C(22B)-C(23B) | 124.4(6) |
| C(22B)-C(23B)-C(18B) | 117.2(6) |
| C(22B)-C(23B)-C(30B) | 115.8(6) |
| C(18B)-C(23B)-C(30B) | 127.0(6) |
| C(19B)-C(24B)-C(25B) | 112.3(5) |
| C(19B)-C(24B)-C(26B) | 109.3(5) |
| C(25B)-C(24B)-C(26B) | 110.8(5) |
| C(21B)-C(27B)-C(28B) | 111.2(6) |
| C(21B)-C(27B)-C(29B) | 111.1(5) |
| C(28B)-C(27B)-C(29B) | 110.6(6) |
| C(23B)-C(30B)-C(31B) | 113.5(5) |
| C(23B)-C(30B)-C(32B) | 109.3(6) |
| C(31B)-C(30B)-C(32B) | 110.4(5) |

Figure 9

Torsion angles [°] for WX-671.2

| | | | |
|---|---|---|---|
| C(6A)-C(1A)-C(2A)-C(3A) | -0.5(11) | C(8A)-C(9A)-C(10A)-N(3A) | -81.2(8) |
| C(8A)-C(1A)-C(2A)-C(3A) | 178.3(6) | C(10A)-N(3A)-C(11A)-C(12A) | -114.5(7) |
| C(1A)-C(2A)-C(3A)-C(4A) | -1.0(11) | C(14A)-N(3A)-C(11A)-C(12A) | 58.6(8) |
| C(1A)-C(2A)-C(3A)-C(7A) | -179.9(7) | C(15A)-N(4A)-C(12A)-C(11A) | -148.4(7) |
| C(2A)-C(3A)-C(4A)-C(5A) | 1.1(11) | C(13A)-N(4A)-C(12A)-C(11A) | 53.3(9) |
| C(7A)-C(3A)-C(4A)-C(5A) | 180.0(7) | N(3A)-C(11A)-C(12A)-N(4A) | -53.8(8) |
| O(5A)-S(1A)-N(5A)-C(9A) | -57.5(5) | C(15A)-N(4A)-C(13A)-C(14A) | 146.9(7) |
| O(6A)-S(1A)-N(5A)-C(9A) | 175.2(5) | C(12A)-N(4A)-C(13A)-C(14A) | -53.8(9) |
| C(18A)-S(1A)-N(5A)-C(9A) | 59.8(5) | C(10A)-N(3A)-C(14A)-C(13A) | 114.5(7) |
| C(3A)-C(4A)-C(5A)-C(6A) | 0.4(12) | C(11A)-N(3A)-C(14A)-C(13A) | -58.1(8) |
| C(2A)-C(1A)-C(6A)-C(5A) | 2.0(11) | N(4A)-C(13A)-C(14A)-N(3A) | 53.1(8) |
| C(8A)-C(1A)-C(6A)-C(5A) | -176.8(7) | C(16A)-O(4A)-C(15A)-O(3A) | -8.1(14) |
| C(4A)-C(5A)-C(6A)-C(1A) | -1.9(11) | C(16A)-O(4A)-C(15A)-N(4A) | 170.7(9) |
| O(1A)-N(2A)-C(7A)-N(1A) | 8.5(12) | C(13A)-N(4A)-C(15A)-O(3A) | -13.0(12) |
| O(1A)-N(2A)-C(7A)-C(3A) | -168.6(7) | C(12A)-N(4A)-C(15A)-O(3A) | -170.9(8) |
| O(1A')-N(1A)-C(7A)-N(2A) | 40(4) | C(13A)-N(4A)-C(15A)-O(4A) | 168.2(7) |
| O(1A')-N(1A)-C(7A)-C(3A) | -143(4) | C(12A)-N(4A)-C(15A)-O(4A) | 10.3(11) |
| C(2A)-C(3A)-C(7A)-N(2A) | 152.6(8) | C(15A)-O(4A)-C(16A)-C(17A) | 158.6(10) |
| C(4A)-C(3A)-C(7A)-N(2A) | -26.3(12) | O(5A)-S(1A)-C(18A)-C(19A) | 10.6(6) |
| C(2A)-C(3A)-C(7A)-N(1A) | -24.6(12) | O(6A)-S(1A)-C(18A)-C(19A) | 141.6(5) |
| C(4A)-C(3A)-C(7A)-N(1A) | 156.6(8) | N(5A)-S(1A)-C(18A)-C(19A) | -104.8(5) |
| C(2A)-C(1A)-C(8A)-C(9A) | -85.0(8) | O(5A)-S(1A)-C(18A)-C(23A) | -168.3(4) |
| C(6A)-C(1A)-C(8A)-C(9A) | 93.7(8) | O(6A)-S(1A)-C(18A)-C(23A) | -37.2(5) |
| S(1A)-N(5A)-C(9A)-C(10A) | -90.1(6) | N(5A)-S(1A)-C(18A)-C(23A) | 76.3(5) |
| S(1A)-N(5A)-C(9A)-C(8A) | 151.2(5) | C(23A)-C(18A)-C(19A)-C(20A) | 4.2(8) |
| C(1A)-C(8A)-C(9A)-N(5A) | -64.4(7) | S(1A)-C(18A)-C(19A)-C(20A) | -174.7(4) |
| C(1A)-C(8A)-C(9A)-C(10A) | 175.9(6) | C(23A)-C(18A)-C(19A)-C(24A) | -177.5(5) |
| C(11A)-N(3A)-C(10A)-O(2A) | -4.4(10) | S(1A)-C(18A)-C(19A)-C(24A) | 3.7(8) |
| C(14A)-N(3A)-C(10A)-O(2A) | -176.5(6) | C(18A)-C(19A)-C(20A)-C(21A) | -1.0(9) |
| C(11A)-N(3A)-C(10A)-C(9A) | 174.3(6) | C(24A)-C(19A)-C(20A)-C(21A) | -179.5(6) |
| C(14A)-N(3A)-C(10A)-C(9A) | 2.2(10) | C(19A)-C(20A)-C(21A)-C(22A) | -2.6(10) |
| N(5A)-C(9A)-C(10A)-O(2A) | -21.9(9) | C(19A)-C(20A)-C(21A)-C(27A) | -179.6(6) |
| C(8A)-C(9A)-C(10A)-O(2A) | 97.4(7) | C(20A)-C(21A)-C(22A)-C(23A) | 3.1(9) |
| N(5A)-C(9A)-C(10A)-N(3A) | 159.5(6) | C(27A)-C(21A)-C(22A)-C(23A) | -179.9(6) |

Figure 9 (continued)

| | | | |
|---|---|---|---|
| C(21A)-C(22A)-C(23A)-C(18A) | 0.0(9) | C(2B)-C(1B)-C(8B)-C(9B) | -98.9(8) |
| C(21A)-C(22A)-C(23A)-C(30A) | 179.4(6) | C(6B)-C(1B)-C(8B)-C(9B) | 82.0(9) |
| C(19A)-C(18A)-C(23A)-C(22A) | -3.7(8) | S(1B)-N(5B)-C(9B)-C(10B) | -93.8(6) |
| S(1A)-C(18A)-C(23A)-C(22A) | 175.2(4) | S(1B)-N(5B)-C(9B)-C(8B) | 148.8(5) |
| C(19A)-C(18A)-C(23A)-C(30A) | 176.9(6) | C(1B)-C(8B)-C(9B)-N(5B) | -73.8(8) |
| S(1A)-C(18A)-C(23A)-C(30A) | -4.2(8) | C(1B)-C(8B)-C(9B)-C(10B) | 168.5(6) |
| C(20A)-C(19A)-C(24A)-C(26A) | -39.9(8) | C(14B)-N(3B)-C(10B)-O(2B) | -176.7(7) |
| C(18A)-C(19A)-C(24A)-C(26A) | 141.7(6) | C(11B)-N(3B)-C(10B)-O(2B) | -3.6(10) |
| C(20A)-C(19A)-C(24A)-C(25A) | 81.9(7) | C(14B)-N(3B)-C(10B)-C(9B) | -1.1(10) |
| C(18A)-C(19A)-C(24A)-C(25A) | -96.5(7) | C(11B)-N(3B)-C(10B)-C(9B) | 172.0(6) |
| C(22A)-C(21A)-C(27A)-C(28A) | -110.2(7) | N(5B)-C(9B)-C(10B)-O(2B) | -22.9(9) |
| C(20A)-C(21A)-C(27A)-C(28A) | 66.7(8) | C(8B)-C(9B)-C(10B)-O(2B) | 95.0(7) |
| C(22A)-C(21A)-C(27A)-C(29A) | 127.6(6) | N(5B)-C(9B)-C(10B)-N(3B) | 161.5(6) |
| C(20A)-C(21A)-C(27A)-C(29A) | -55.5(8) | C(8B)-C(9B)-C(10B)-N(3B) | -80.7(8) |
| C(22A)-C(23A)-C(30A)-C(32A) | -76.7(7) | C(10B)-N(3B)-C(11B)-C(12B) | -116.8(7) |
| C(18A)-C(23A)-C(30A)-C(32A) | 102.7(7) | C(14B)-N(3B)-C(11B)-C(12B) | 57.1(8) |
| C(22A)-C(23A)-C(30A)-C(31A) | 45.8(8) | C(15B)-N(4B)-C(12B)-C(11B) | -130.5(7) |
| C(18A)-C(23A)-C(30A)-C(31A) | -134.8(6) | C(13B)-N(4B)-C(12B)-C(11B) | 54.3(9) |
| C(6B)-C(1B)-C(2B)-C(3B) | -0.6(11) | N(3B)-C(11B)-C(12B)-N(4B) | -53.0(8) |
| C(8B)-C(1B)-C(2B)-C(3B) | -179.7(6) | C(15B)-N(4B)-C(13B)-C(14B) | 130.5(7) |
| C(1B)-C(2B)-C(3B)-C(4B) | -4.0(11) | C(12B)-N(4B)-C(13B)-C(14B) | -54.1(9) |
| C(1B)-C(2B)-C(3B)-C(7B) | 172.9(7) | C(10B)-N(3B)-C(14B)-C(13B) | 116.7(7) |
| C(2B)-C(3B)-C(4B)-C(5B) | 6.4(11) | C(11B)-N(3B)-C(14B)-C(13B) | -56.8(8) |
| C(7B)-C(3B)-C(4B)-C(5B) | -170.4(7) | N(4B)-C(13B)-C(14B)-N(3B) | 52.7(8) |
| O(5B)-S(1B)-N(5B)-C(9B) | -61.4(5) | C(16B)-O(4B)-C(15B)-O(3B) | -3.4(10) |
| O(6B)-S(1B)-N(5B)-C(9B) | 172.1(5) | C(16B)-O(4B)-C(15B)-N(4B) | 175.3(6) |
| C(18B)-S(1B)-N(5B)-C(9B) | 56.5(5) | C(13B)-N(4B)-C(15B)-O(3B) | -5.3(11) |
| C(3B)-C(4B)-C(5B)-C(6B) | -4.4(12) | C(12B)-N(4B)-C(15B)-O(3B) | 179.8(7) |
| C(4B)-C(5B)-C(6B)-C(1B) | -0.3(13) | C(13B)-N(4B)-C(15B)-O(4B) | 176.0(6) |
| C(2B)-C(1B)-C(6B)-C(5B) | 2.7(12) | C(12B)-N(4B)-C(15B)-O(4B) | 1.0(10) |
| C(8B)-C(1B)-C(6B)-C(5B) | -178.2(7) | C(15B)-O(4B)-C(16B)-C(17B) | 179.8(6) |
| O(1B)-N(2B)-C(7B)-N(1B) | 1.3(10) | O(5B)-S(1B)-C(18B)-C(23B) | -166.8(4) |
| O(1B)-N(2B)-C(7B)-C(3B) | -177.9(6) | O(6B)-S(1B)-C(18B)-C(23B) | -36.5(5) |
| C(4B)-C(3B)-C(7B)-N(1B) | -32.0(11) | N(5B)-S(1B)-C(18B)-C(23B) | 77.6(5) |
| C(2B)-C(3B)-C(7B)-N(1B) | 151.2(7) | O(5B)-S(1B)-C(18B)-C(19B) | 11.2(6) |
| C(4B)-C(3B)-C(7B)-N(2B) | 147.2(7) | O(6B)-S(1B)-C(18B)-C(19B) | 141.5(5) |
| C(2B)-C(3B)-C(7B)-N(2B) | -29.6(10) | N(5B)-S(1B)-C(18B)-C(19B) | -104.4(5) |
| | | C(23B)-C(18B)-C(19B)-C(20B) | 3.6(9) |

Figure 9 (continued)

| | |
|---|---|
| S(1B)-C(18B)-C(19B)-C(20B) | -174.4(5) |
| C(23B)-C(18B)-C(19B)-C(24B) | -176.8(6) |
| S(1B)-C(18B)-C(19B)-C(24B) | 5.3(8) |
| C(18B)-C(19B)-C(20B)-C(21B) | 1.9(10) |
| C(24B)-C(19B)-C(20B)-C(21B) | -177.8(6) |
| C(19B)-C(20B)-C(21B)-C(22B) | -6.1(10) |
| C(19B)-C(20B)-C(21B)-C(27B) | 178.3(6) |
| C(20B)-C(21B)-C(22B)-C(23B) | 5.2(10) |
| C(27B)-C(21B)-C(22B)-C(23B) | -179.2(6) |
| C(21B)-C(22B)-C(23B)-C(18B) | -0.1(10) |
| C(21B)-C(22B)-C(23B)-C(30B) | 179.5(6) |
| C(19B)-C(18B)-C(23B)-C(22B) | -4.4(9) |
| S(1B)-C(18B)-C(23B)-C(22B) | 173.6(5) |
| C(19B)-C(18B)-C(23B)-C(30B) | 176.0(6) |
| S(1B)-C(18B)-C(23B)-C(30B) | -5.9(8) |
| C(20B)-C(19B)-C(24B)-C(25B) | -41.4(8) |
| C(18B)-C(19B)-C(24B)-C(25B) | 138.9(6) |
| C(20B)-C(19B)-C(24B)-C(26B) | 82.0(7) |
| C(18B)-C(19B)-C(24B)-C(26B) | -97.7(7) |
| C(22B)-C(21B)-C(27B)-C(28B) | 127.4(7) |
| C(20B)-C(21B)-C(27B)-C(28B) | -57.2(8) |
| C(22B)-C(21B)-C(27B)-C(29B) | -109.0(7) |
| C(20B)-C(21B)-C(27B)-C(29B) | 66.3(8) |
| C(22B)-C(23B)-C(30B)-C(31B) | 47.3(8) |
| C(18B)-C(23B)-C(30B)-C(31B) | -133.2(6) |
| C(22B)-C(23B)-C(30B)-C(32B) | -76.4(7) |
| C(18B)-C(23B)-C(30B)-C(32B) | 103.1(7) |

Micrograph of WX-671 after crystallization from acetonitrile in the freezer

CRYSTALLINE MODIFICATIONS OF N-ALPHA-(2,4,6-TRIISOPROPYLPHENYLSULFONYL)-3-HYDROXYAMIDINO-(L)- PHENYLALANINE 4-ETHOXYCARBONYLPIPERAZIDE AND/OR SALTS THEREOF

CROSS-REFERENCE TO RELATED APPLICATIONS

This application is a divisional of prior application Ser. No. 11/664,266 filed Mar. 30, 2007, which is a National Stage Entry and claims the benefit of PCT/EP05/12589 filed Nov. 24, 2005, the entire disclosure of which is incorporated herein by reference.

The present invention relates to novel crystalline modifications of N-α-(2,4,6-triisopropylphenyl-sulfonyl)-3-hydroxyamidino-(L)-phenylalanine 4-ethoxy-carbonylpiperazide and/or salts thereof, which can be used as pharmaceutical agents, and to pharmaceutical compositions and pharmaceutical uses comprising these novel crystalline modifications.

The novel crystalline modifications of the present invention, which start from a compound which is known under the chemical name N-α-(2,4,6-triisopropylphenyl-sulfonyl)-3-hydroxyamidino-(L)-phenylalanine 4-ethoxy-carbonylpiperazide, are efficacious inhibitors of serine protease urokinase and therefore particularly suitable for the treatment of urokinase-associated disorders, such as, for example, tumors and metastases, in particular for oral use. The free base form is designated as WX-671.

The plasminogen activator of the urokinase type (uPA) plays a key role in tumor invasion and formation of metastases (Schmitt et al., J. Obst. Gyn. 21 (1995), 151-165). uPA is expressed in the most different types of tumor cells (Kwaan, Cancer Metastasis Rev. 11 (1992), 291-3.11) and binds to the tumo-associated uPA receptor (uPAR), where the activation of plasminogen to plasmin takes place. Plasmin is able to break down various components of the extracellular matrix (ECM), such as fibronectin, laminin and collagen type IV. It also activates some other ECM-degrading enzymes, in particular matrix metalloproteinases. High amounts of tumor-associated uPA correlate with a higher risk of metastasis for cancer patients (Harbeck et al., Cancer Research 62 (2002), 4617-4622). Inhibition of the proteolytic activity of uPA is therefore a good starting point for an antimetastatic therapy.

A few active and selective urokinase inhibitors have already been described. Thus, uPA inhibitors of the benzamidine type are disclosed in EP 1 098 651, uPA inhibitors of the arylguanidine type in WO 01/96286 and WO 02/14349. A common feature of these synthetic inhibitors is a basic residue consisting of an amidino or/and guanidino group.

International patent application WO 03/072559 discloses WX-671 as an intermediate in the synthesis of the urokinase inhibitor N-α-(2,4,6-triisopropylphenyl-sulfonyl)-3-amidino-(L)-phenylalanine 4-ethoxy-carbonylpiperazide. WO 03/072559 also discloses a process for the preparation of the compound WX-671 as a free base or in the form of its salts formed with acids. Special salts, in particular the hydrogensulfate and the sulfate form, are not mentioned. Process for crystallization are likewise not described. In the processes described, the free base WX-671 is obtained as an amorphous product, which is thermally slightly unstable and hygroscopic and which has unsuitable filtration and drying properties. For this reason, it is not suitable for preparation on a large scale and must be especially protected from heat and moisture.

WO 2004/011449 likewise discloses processes for the p-3-hydroxymamidine derivatives, which can also be present as salts, e.g. as salts of mineral acids or as salts of organic acids. One of the compounds prepared is WX-671. Here too, no indication is given of the fact that the compounds disclosed can also be obtained in a stable crystalline form. PCT/EP2004/005682 discloses hydroxyamine and hydroxyguanidine compounds as urokinase inhibitors. The medicaments disclosed comprise as active compound, inter alia, WX-671 and the active compounds can be present as salts, e.g. as hydrochloride or hydrogensulfate or as salts of organic acids. A better bioavailability on oral administration was asserted for the medicaments claimed there. This publication too, however, does not disclose any sulfate salt compound of said urokinase inhibitors.

The object of the present invention was the preparation of crystalline modifications of N-α-(2,4,6-tri-isopropylphenyl-sulfonyl)-3-hydroxyamidino-(L)-phenyl-alanine 4-ethoxy-carbonylpiperazide and/or salts thereof, which have advantageous properties compared to the compounds of the prior art.

The present invention provides crystalline modifications of N-α-(2,4,6-triisopropylphenyl-sulfonyl)-3-hydroxyamidino-(L)-phenylalanine 4-ethoxy-carbonylpiperazide and/or salts thereof.

According to the present invention, novel crystalline modifications of the abovementioned urokinase inhibitor were found which have crucial advantages compared to the amorphous form of this compound. The crystalline modifications according to the invention have important advantages in handling, storage and formulation.

Surprisingly, the compound N-α-(2,4,6-triisopropyl-phenylsulfonyl)-3-hydroxyamidino-(L)-phenylalanine 4-ethoxycarbonylpiperazide and/or salts thereof can be crystallized, which was not possible hitherto, and is therefore superior in its properties to the amorphous compounds from the prior art. Thus the crystalline modifications according to the invention are distinguished by very low hygroscopicity. They are moreover very resistant to decomposition and are therefore also suitable for longer storage. In addition, the crystalline modifications according to the invention have improved filtration and drying properties. Moreover, the crystalline modifications of N-α-(2,4,6-triisopropylphenylsulfonyl)-3-hydroxy-amidino-(L)-phenylalanine 4-ethoxycarbonylpiperazide and its salts are ideally suitable for formulation in pharmaceutical compositions.

As used herein, WX-671 means the free base of N-α-(2,4,6-triisopropylphenylsulfonyl)-3-hydroxyamidino-(L)-phenylalanine 4-ethoxycarbonylpiperazide. WX-671.1 designates the hydrogensulfate of said compound and WX-671.2 designates the sulfate of said compound.

As already mentioned at the outset, the modifications of WX-671 according to the invention and salts thereof are essentially crystalline. Hitherto, it was not possible to prepare hydroxyamidine compounds of this type in crystalline form. Even the compounds already disclosed in the prior art were not crystallizable.

The crystalline modifications, according to the invention of N-α-(2,4,6-triisopropylphenylsulfonyl)-3-hydroxyamidino-(L)-phenylalanine 4-ethoxycarbonyl-piperazide and its salts preferably include the hydrogensulfate salt (WX-671.1) and the sulfate salt (WX-671.2), and the free base (WX-671).

The crystalline modifications according to the invention can include mixtures of the free base and of the salts or alternatively mixtures of the salts. Preferably, the crystalline modification according to the invention in each case includes either the free base or the sulfate salt or the hydrogensulfate salt as a crystalline modification. Particularly preferably, the crystalline modification according to the invention includes single crystals of the respective crystalline modification.

The crystalline modifications according to the invention were investigated by X-ray diffractometry and preferably have the peaks shown in Table 3.1 (for the sulfate salt WX-671.2), Table 7.1 (for the hydrogen-sulfate salt WX-671.1) and Table 11.1 (for the free base). The crystalline modifications according to the invention essentially have the peaks shown in FIGS. 5 (for the sulfate salt WX-671.2), 13 (for the hydrogen-sulfate salt WX-671.1) and 19 (for the free base).

As is described in the examples below, additionally to the X-ray diffractometry analyses, thermoanalytical investigations were also carried out (differential scanning calorimetry, DSC and thermogravimetry, TGA). It was seen here that the crystalline compound of the hydrogensulfate salt WX-671.1 decomposes at a temperature of approximately 175° C.-195° C., more precisely in the range from approximately 185° C. (at a heating rate of 2 Kmin$^{-1}$).

The crystalline modification of WX-671.2 according to the invention preferably contains N-α-(2,4,6-tri-isopropylphenylsulfonyl)-3-hydroxyamidino-(L)-phenyl-alanine 4-ethoxycarbonylpiperazide and sulfate anions in a molar ratio of approximately 2:1, where this ratio can vary in a range from 1.5 to 2.5:1. A ratio of approximately 1.25 to 2.25:1 is preferred, more highly preferably 1.1 to 2.1:1 and most highly preferably in the ratio of approximately 2:1.

The crystalline modification of WX-671.2 preferably has units of in each case 2 molecules of N-α-(2,4,6-tri-isopropylphenylsulfonyl)-3-hydroxyamidino-(L)-phenyl-alanine 4-ethoxycarbonylpiperazide and a sulfate anion, where in each of these units the 2 molecules of N-α-(2,4,6-triisopropylphenylsulfonyl)-3-hydroxyamidino-(L)-phenylalanine 4-ethoxycarbonylpiperazide can be present in the same conformation or they can preferably also be present in different conformations.

In addition, the crystalline modification of WX-671.2 is preferably present as a hydrate, in particular as a trihydrate, i.e. per mole of salt approximately 3 mol of water are present. This ratio can, of course, also be subject to slight variations, i.e. per mole of salt on average between 2.5 and 3.5 mol of water can be present, preferably between 2.25 and 3.25, more highly preferably between 2.2 and 3.2, more highly preferably between 2.1 and 3.1.

The sulfate salt of N-α-(2,4,6-triisopropylphenyl-sulfonyl)-3-hydroxyamidino-(L)-phenylalanine 4-ethoxy-carbonylpiperazide has, independently of the crystallinity, turned out to be the thermodynamically stable compound. Therefore the present invention also provides the novel compound of N-α-(2,4,6-tri-isopropylphenylsulfonyl)-3-hydroxyamidino-(L)-phenyl-alanine 4-ethoxycarbonylpiperazide sulfate salt. The noncrystalline sulfate salt WX-671.2 is also suitable, as described below for the crystalline modifications, for the production of medicaments.

In the crystalline modification of WX-671.1, N-α-(2,4,6-triisopropylphenylsulfonyl)-3-hydroxyamidino-(L)-phenylalanine 4-ethoxycarbonylpiperazide and hydrogensulfate anions are preferably present in a molar ratio of 0.5 to 1.5:1, more highly preferably of 0.8 to 1.2:1, more highly preferably 0.9 to 1.1:1, more highly preferably approximately 1:1.

A crystalline modification of WX-671.1 can also be present as a hydrate.

The crystalline modification of WX-671 (free base) is preferably not present as a hydrate. A hydrate form is, however, possible.

The crystalline modifications according to the invention can optionally be used with suitable pharmaceutical excipients and/or vehicles for the production of medicaments. Here, administration in combination with other active compounds, e.g. other urokinase inhibitors, such as, for example, antibodies and/or peptides, but also with chemotherapeutics and cytostatics or/and other cytostatic and cytotoxic active compounds is possible.

The crystalline modifications according to the invention can thus be prepared in a suitable pharmaceutical formulation, for example as tablets, coated tablets, capsules, pastilles, powder, syrup, suspension, solution or the like. In particular, a pharmaceutical preparation for oral administration is preferred.

The crystalline modifications according to the invention are suitable for the control of diseases which are associated with a pathological overexpression of uPA or/and urokinase plasminogen activator receptor (uPAR). It is, for example, able to inhibit the growth or/and the spread of malignant tumors and the metastasis of tumors highly efficiently. Examples of this are oncoses, e.g. breast cancer, lung cancer, bladder cancer, stomach cancer, cervical cancer, ovarian cancer, kidney cancer, prostate cancer and soft tissue sarcomas, in particular tumors associated with a high metastasis rate.

The modifications according to the invention can be employed on their own or in combination with other physiologically active substances, e.g. with radiotherapeutics or with cytotoxic or/and cytostatic agents, e.g. chemotherapeutics, such as, for example, cis-platin, doxorubicin, 5-fluorouracil, taxol derivatives, or/and other chemotherapeutic agents, for example selected from the group consisting of the alkylating agents, antimetabolites, antibiotics, epidophyllotoxins and vinca alkaloids. A combination with radiation therapy or/and surgical interventions is likewise possible.

Furthermore, the crystalline modifications according to the invention are also efficacious for other uPA-associated diseases. Examples of diseases of this type are, for example, pulmonary high blood pressure and/or heart diseases (e.g. WO 02/00248), gastric and bowel diseases, such as, for example, inflammatory bowel diseases, premalignant colon adenomas, inflammatory diseases, such as, for example, septic arthritis, or other diseases, such as osteoporosis, cholesteatomy, skin and eye diseases, such as, for example, age-related macular degeneration (AMD), and viral or bacterial infections, reference being made expressly to the diseases mentioned in EP-A-0 691 350, EP-A-1 182 207 and U.S. Pat. No. 5,712,291.

A further subject of the present invention is a medicament which includes a crystalline modification according to the invention as an active compound. Such a medicament can optionally additionally include pharmaceutically tolerable carriers and/or excipients. The medicaments can be administered to man or animals topically, orally, rectally or parenterally, e.g. intravenously, subcutaneously, intramuscularly, intraperitoneally, or alternatively sublingually, nasally and/or inhalatively. Suitable administration forms are, for example, tablets, coated tablets, capsules, pastilles, pellets, powder, suppositories, solutions, syrup, emulsions, suspensions, liposomes, inhalation sprays or transdermal systems, such as, for example, patches. A particularly preferred pharmaceutical compositions is suitable for oral administration, e.g. also as a slow-release depot.

In addition, the present invention provides a use of the crystalline modifications according to the invention for the production of pharmaceutical composition for the control of diseases which are associated with a pathological overexpression of urokinase and/or the urokinase receptor. In particular, such a medicament containing the active compound according to the invention is suitable for tumor treatment and/or prevention and in particular also for the treatment or prevention of formation of metastases, and for the treatment of primary tumors and secondary tumors.

By means of the present invention, one possibility for urokinase inhibition in living beings, in particular man, is provided by administration of an efficacious amount of the modification according to the invention. The dose to be administered depends on the nature and severity of the diseases to be treated. For example, the daily dose is in the range from 0.01-100 mg/kg of active substance per body weight, more highly preferably 0.1-50 mg/kg, more highly preferably 0.5-40 mg/kg, more highly preferably 1-30 mg/kg, more highly preferably 5-25 mg/kg.

A further subject of the present invention is a process for the production of an essentially crystalline modification of an N-α-(2,4,6-triisopropylphenyl-sulfonyl)-3-hydroxyamidino-(L)-phenylalanine 4-ethoxy-carbonylpiperazide salt, comprising the steps:
(a) preparation of the compound N-α-(2,4,6-tri-isopropylphenylsulfonyl)-3-hydroxyamidino-(L)-phenylalanine 4-ethoxycarbonylpiperazide or of one of its salts,
(b) dissolution or/and suspension of the compound or of the salt itself from step (a) in a solvent suitable for the formation of the crystalline modification,
(c) separation of the crystalline modification.

It has surprisingly been shown that the crystalline modifications of WX-671, WX-671.1 and WX-671.2 can be prepared in crystalline form in a simple manner. Preferably, the starting material used is a salt of N-α-(2,4,6-triisopropylphenylsulfonyl)-3-hydroxyamidino-(L)-phenylalanine 4-ethoxycarbonylpiperazide, particularly preferably the hydrogensulfate salt.

However, other salt compounds are also suitable as starting compounds for the formation of crystalline modifications, for example the besylate salt, hydrochloride salt, mesylate salt, tartrate salt and others.

Solvents used for step (b) can preferably be various organic solvents. Those suitable are, for example, water and various alcohols, e.g. methanol, ethanol, propanol, butanol and their isoforms, such as, for example, isopropanol, isobutanol etc., and furthermore glycols, ethers, glycol ethers, acetone and the like. Further suitable solvents are tetrahydrofuran (THF) and acetonitrile. Preferred solvents are in particular acetone and acetonitrile.

However, water can also be used as a solvent. In particular for the recrystallization (see step (d)), water is preferably used.

If the free base is used as a starting material for the preparation of a crystalline modification of a salt of N-α-(2,4,6-triisopropylphenylsulfonyl)-3-hydroxy-amidino-(L)-phenylalanine 4-ethoxycarbonylpiperazide, suitable salts or acids are additionally added in step (b) in order to obtain the respective desired salt of N-α-(2,4,6-triisopropylphenylsulfonyl)-3-hydroxy-amidino-(L)-phenylalanine 4-ethoxycarbonylpiperazide.

The process according to the invention can also include a further step (d) of recrystallizing the crystalline compounds from step (c). This applies in particular for the preparation of WX-671.2 from WX-671.1. Here, the crystalline modification resulting in step (c) is in turn preferably recrystallized in a suitable solvent or a mixture of solvents. Here too, as solvents those mentioned beforehand can be employed. In particular, water is preferred, or recrystallization is preferably carried out with a content of water sufficient for the formation of the desired crystalline modification. Water is preferred in particular if, as, for example, in the case of WX-671.2, a hydrate (in the case of WX-671.2 a trihydrate) is formed.

The invention will now be illustrated in more detail by the following figures and the examples.

DESCRIPTION OF THE FIGURES

FIG. 7 lists the crystal data and structure refinement for WX-671.2.

FIG. 8 shows the bond lengths [Å] and angles [°] for WX-671.2.

FIG. 9 shows the torsion angles [°] for WX-671.2.

EXAMPLES

Example 1

Figure 1:
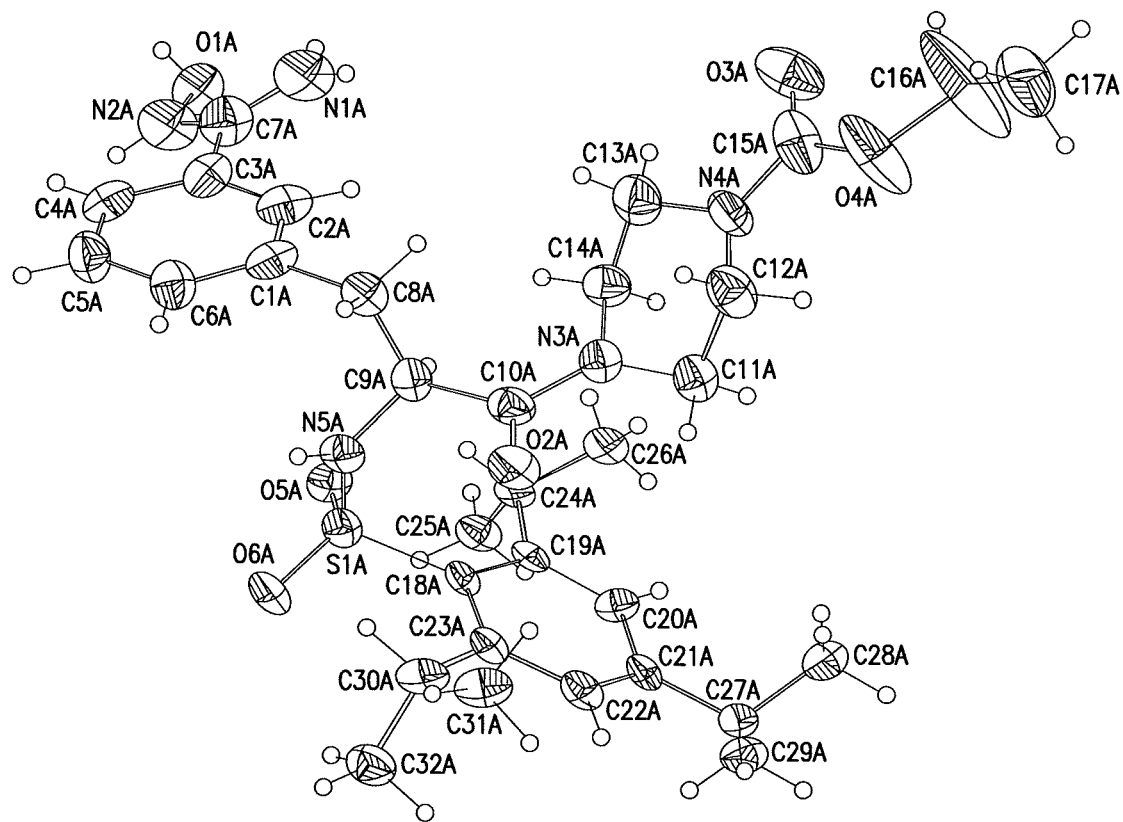
FIG. 1 shows an Ortep plot (50%) with symbol plot for molecule A (WX-671.2).
Figure 2:
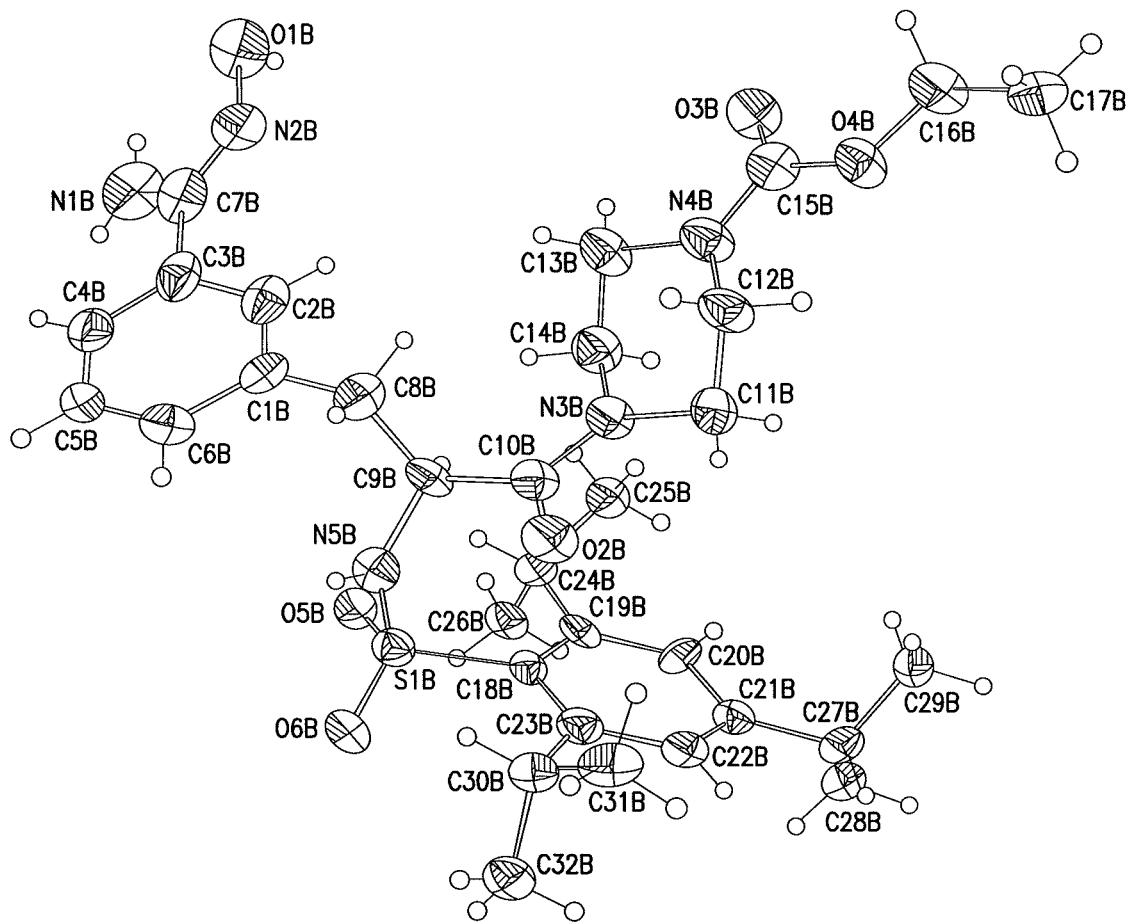
FIG. 2 shows an Ortep plot (50%) with symbol plot for molecule B (WX-671.2).
Figure 3:
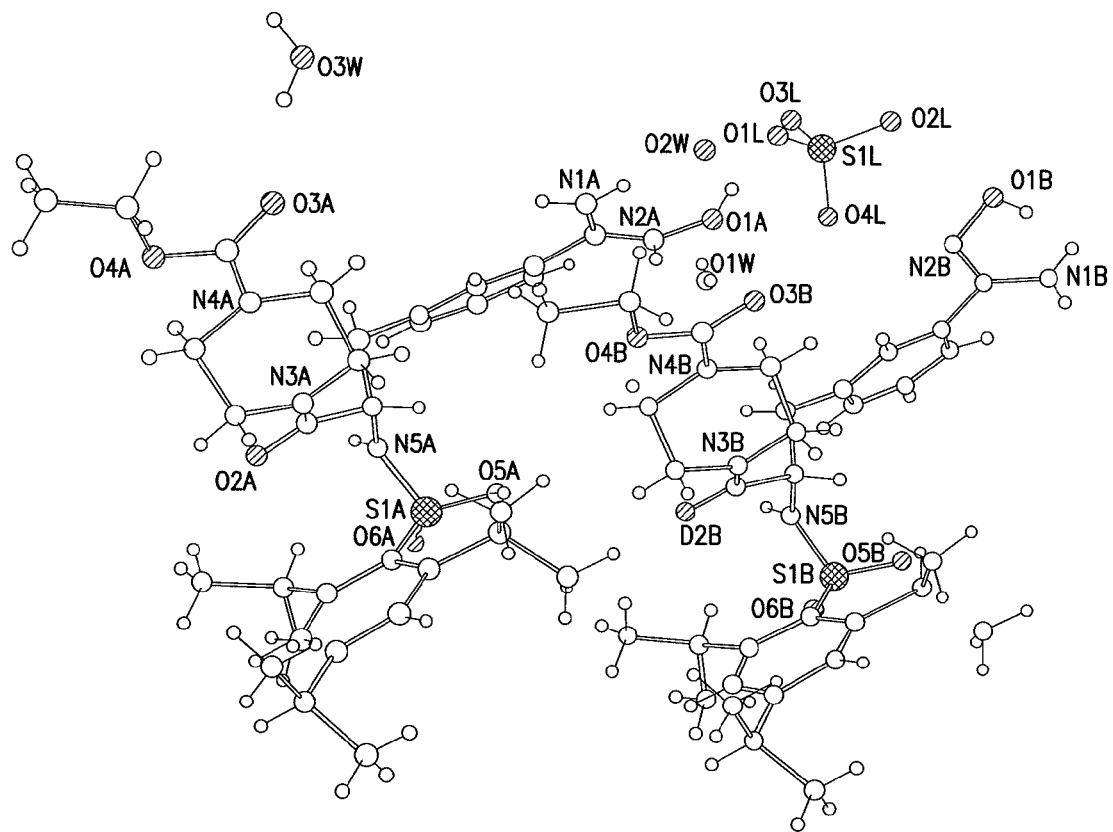
FIG. 3 shows independent molecules within a unit cell of a unit of two molecules of WX-671.2 and sulfate anion.
Figure 4:
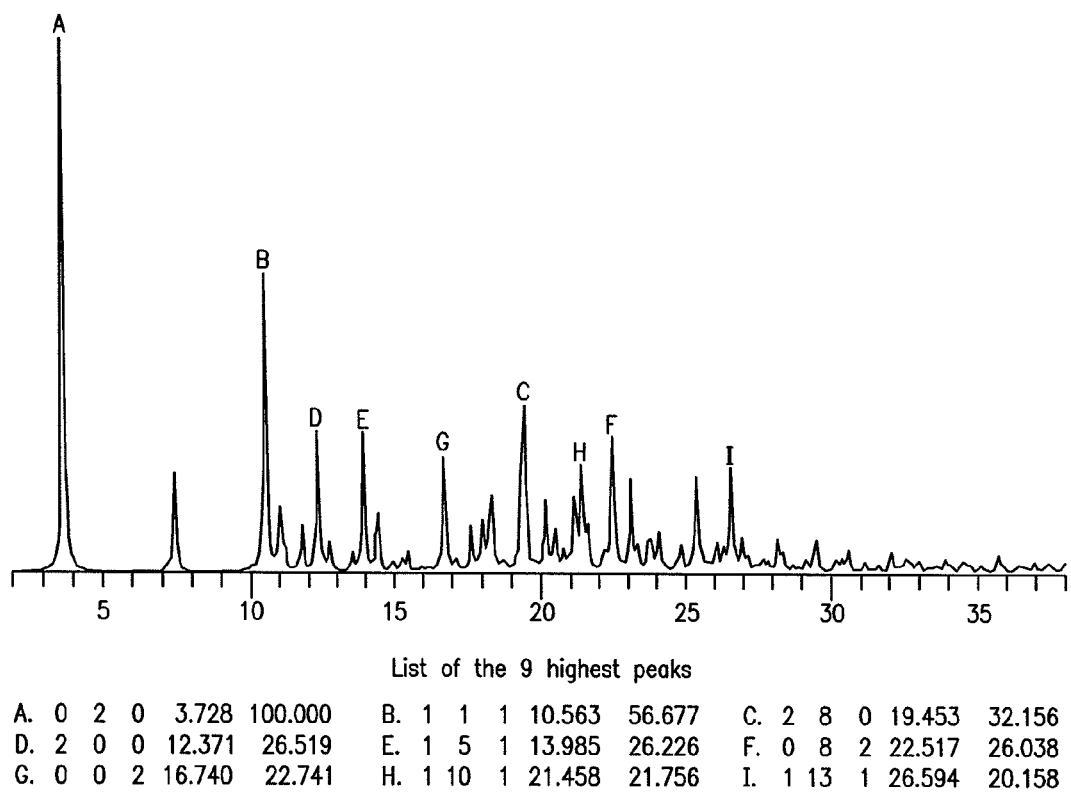
FIG. 4 shows a simulated X-ray diffractogram using single crystal data of WX-671.2.
Figure 5:
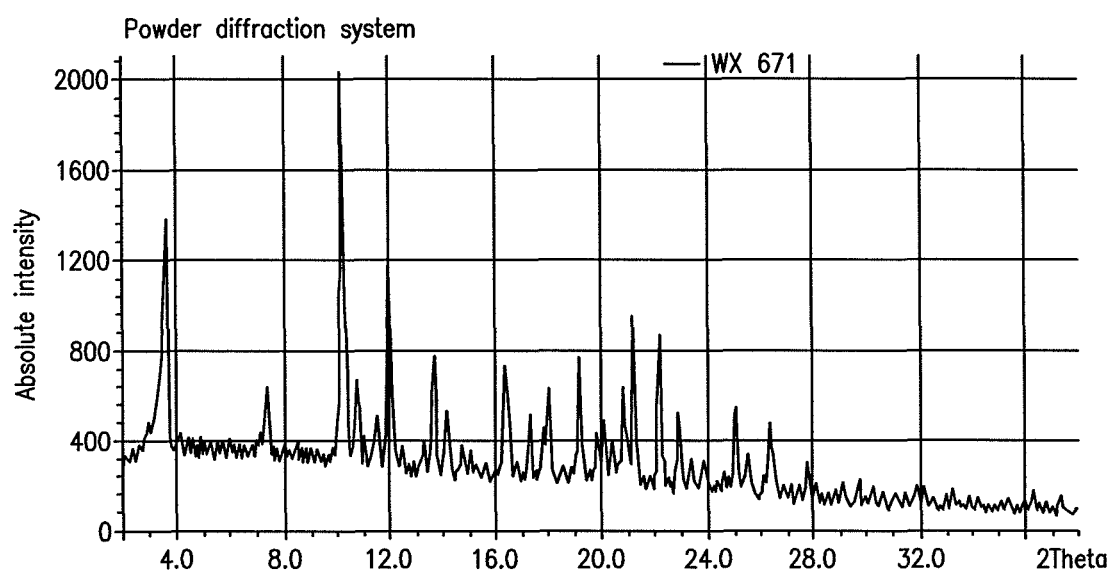
FIG. 5 shows an experimental X-ray diffractogram of WX-671.2.
Figure 6A:
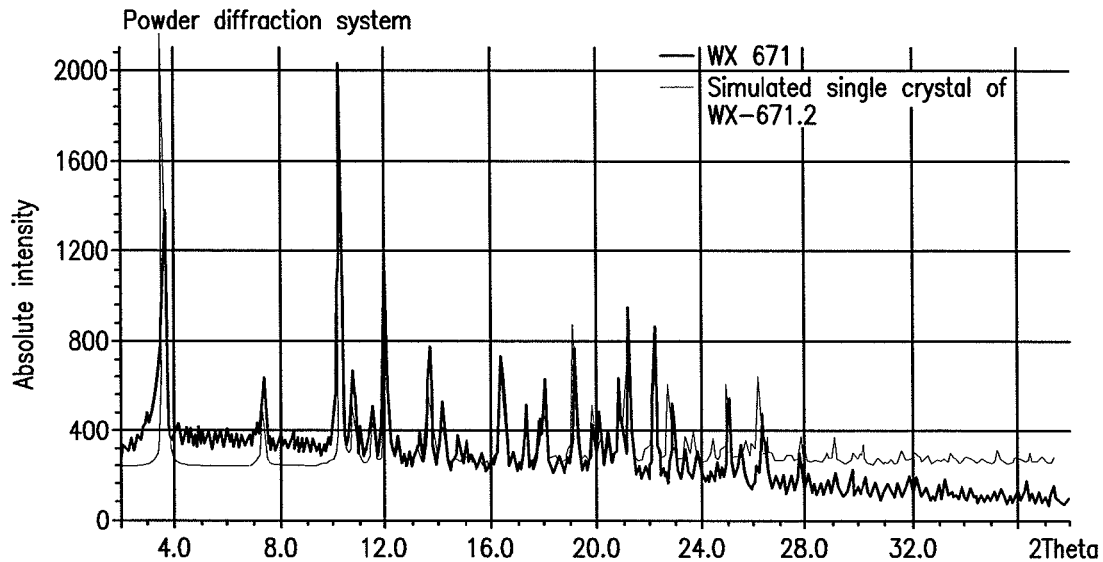
FIG. 6a shows the superimposition of the simulated X-ray diffraction pattern and of the experimental X-ray diffraction pattern according to FIGS. 4 and 5 for WX-671.2.
Figure 6B:
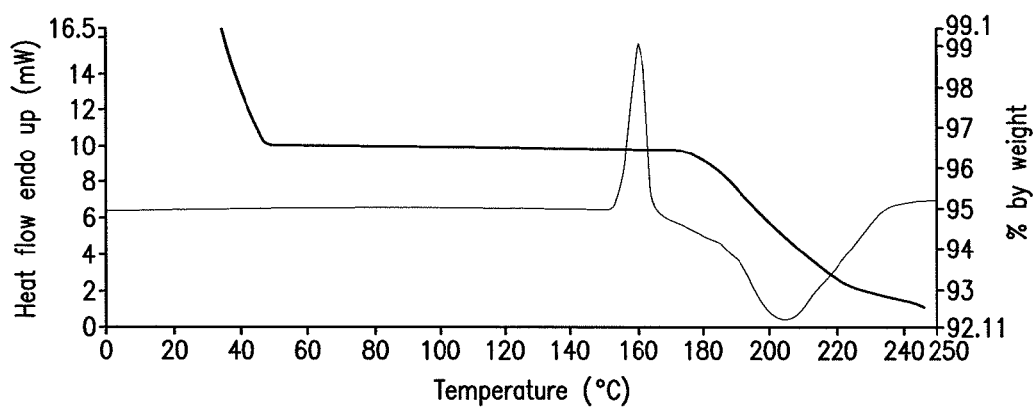
FIG. 6b shows the DSC and TGA thermograms of WX-671.2 after stirring in water.

Preparation of Various Salts of N-α-(2,4,6-tri-isopropylphenylsulfonyl)-3-hydroxyamidino-(L)-phenylalanine 4-ethoxycarbonylpiperazide The salts were prepared by dissolving 6.0 g of WX-671 in 50 ml of acetone. The acids used were added in a 25% excess without dilution and the mixture was stirred at room temperature for two hours.

Crystallization Conditions

TABLE 1.1

| Acid | Equivalent | Crystallization conditions | Drying |
|---|---|---|---|
| HCl | 1.25 mol eq. | Clear solution | High vacuum |
| $H_2SO_4$ | 1.25 mol eq. | Crystallized from acetone solution | High vacuum |
| MsOH | 1.25 mol eq. | Crystallized from acetone solution | High vacuum |
| BsOH | 1.25 mol eq. | Clear solution | High vacuum |
| Tartaric acid | 1.25 mol eq. | Clear solution | High vacuum |

MsOH: methanesulfonic acid;
BsOH: benzenesulfonic acid

In a second step, the salts were suspended for 7 days in a suitable solvent, filtered and dried at room temperature.
Investigation of the Crystallinity
Processes: X-ray diffractometry (XRD); microscopy

TABLE 1.2

| Species | XRD | Microscopy |
|---|---|---|
| Free base | mainly crystalline | small particles |
| Besylate | mainly amorphous | agglomerates |
| Hydrochloride | completely amorphous | small particles |
| Mesylate | liquid crystalline | agglomerates |
| Hydrogensulfate | liquid crystalline | agglomerates |
| Tartrate | completely amorphous | glass |

Investigation of the Hygroscopicity
Process: storage for 1 week/85% relative humidity; thermogravimetric analysis (TGA)

TABLE 1.3

| Species | TGA | |
|---|---|---|
| Free base | 1.5% | (semihydrate) |
| Besylate | 10.1% | (adsorptive) |
| Hydrochloride | 7.5% | (adsorptive) |
| Mesylate | 7.8% | (adsorptive) |
| Hydrogensulfate | 0.8% | (adsorptive) |
| Tartrate | 10.5% | (adsorptive) |

Example 2

Crystallization and Single Crystal X-Ray Structural Analysis of WX-671.2 (Sulfate Salt)

The novel form of N-α-(2,4,6-triisopropylphenyl-sulfonyl)-3-hydroxyamidino-(L)-phenylalanine 4-ethoxy-carbonylpiperazide sulfate is obtained by suspending the hydrogensulfate salt (WX-671.1) of the compound WX-671 in water and by separating off the crystalline compound formed.

Crystalline WX-671.2 was obtained in two different ways:
a) About 50 mg of WX-671.1 were suspended in about 0.5 ml of water. The suspension was allowed to stand at room temperature. After 6 days, the suspension was filtered and the residue was dried in air at room temperature.
b) About 0.2 g of WX-671.1 was suspended in about 2 ml of water. The suspension was shaken at 25° C. After 3 days, the residue was filtered off and the crystals of WX-671.2 were dried in air at room temperature.

The X-ray structure of the crystalline material (WX-671.2) prepared here was determined. Single crystals were also obtained here.

The crystal structure determination was carried out using a Bruker-Nonius diffractometer equipped with a Proteum CCD surface detector, an FR591 rotating anode with CuKα radiation, Montel mirror as a monochromator and a Kryoflex low temperature apparatus (T=90K). Full sphere data determination omega and phi scans. Programs used: Proteum data collection V.1.37 (Bruker-Nonius 2002), data reduction Saint+ version 6.22 (Bruker-Nonius 2001) and absorption correction SADABS V.2.03 (2002). Crystal structure resolution was achieved by means of direct methods as implemented in SHELXTL version 6.10 (Sheldrick, University of Göttingen) and visualized by means of XP program.

Missing atoms were located by means of differential Fourier synthesis and added to the atom list. "Least squares refinement" on F2 over all measured intensities were performed using the program SHELXTL version 6.10 (Sheldrick, University of Göttingen, 2000). All non-hydrogen atoms were "refined" with the inclusion of the "anisotropic displacement parameters".

TABLE 2.1

| Chirality Check* | | |
|---|---|---|
| | Correct structure | Inverted structure |
| Flack parameter (standard deviation) | 0.0298 (0.0282) | 0.9694 (0.0307) |
| Twin Basf (standard deviation) | 0.03 (3) | 0.97 (3) |
| wR2 value (with Flack parameter) | 0.2016 | 0.2219 |
| Chirality | S(C9) | R(C9) |

*H. D. Flack, Acta Cryst., 1983, A39, 876-881
H. D. Flack, G. Bernardinelli, Acta Cryst., 1999, A55, 908-915
H. D. Flack, G. Bernardinelli, J. Appl. Cryst., 2000, 33, 1143-1148

The results of the X-ray structural analysis are shown in FIGS. 1 to 3 and 7 to 9.

Example 3

X-Ray Diffractometry of WX-671.2 (Sulfate Salt)

X-ray diffractograms were obtained using a STOE STADI-P Debye-Scherrer diffractometer, equipped with a position-sensitive detector (PSD, 5°), a germanium [1 1 1] primary monochromator and a CuKα 1.6 kW ceramic X-ray tube (1.5406 Å). Program used: Stoe WinXpow, version 2.03 (2003).

TABLE 3.1

X-ray diffractometry peak list for WX-671.2
WX 671.2
Reflections
2 theta

| |
|---|
| 3.7 |
| 4.2 |
| 7.1 |
| 7.4 |
| 10.3 |
| 10.8 |
| 11.1 |
| 11.6 |
| 12.1 |
| 12.6 |
| 13.3 |
| 13.8 |
| 14.2 |
| 14.8 |
| 15.1 |
| 15.7 |
| 16.4 |

TABLE 3.1-continued

X-ray diffractometry peak list for WX-671.2
WX 671.2
Reflections
2 theta

| |
|---|
| 16.8 |
| 17.3 |
| 17.8 |
| 18.0 |
| 18.6 |
| 19.2 |
| 19.8 |
| 20.1 |
| 20.4 |
| 20.8 |
| 21.0 |
| 21.2 |
| 21.8 |
| 22.2 |
| 22.9 |
| 23.4 |
| 23.9 |
| 24.6 |
| 25.0 |
| 25.5 |
| 26.2 |
| 26.3 |
| 26.5 |
| 26.8 |
| 27.2 |
| 27.5 |
| 27.8 |
| 28.1 |
| 29.1 |
| 29.7 |
| 30.2 |
| 30.6 |
| 31.1 |
| 31.4 |
| 31.9 |
| 32.1 |
| 33.2 |
| 33.8 |
| 34.2 |
| 36.3 |
| 37.3 |

Example 4

Recrystallizations of WX-671.1 (Hydrogensulfate Salt)

WX-671.1 was dissolved in solvents (isopropanol, ethanol, methanol) of different polarity. The solutions were filtered, divided into four, and the solvents were removed at different rates.

WX-671.1 exists in its crystalline form (modification A) and two mesophases B and C. It decomposes from about 185° C. (modification A and mesophase B) or 156° C. (mesophase C). For the demonstration of the crystallinity of modification A, an X-ray structure determination is carried out. Modification A is the thermodynamically stable form at room temperature.

Example 5

Differential Scanning Calorimetry (DSC) and Thermo-Gravimetry (TGA) of WX-671.1 (Hydrogensulfate Salt)

Figure 10:
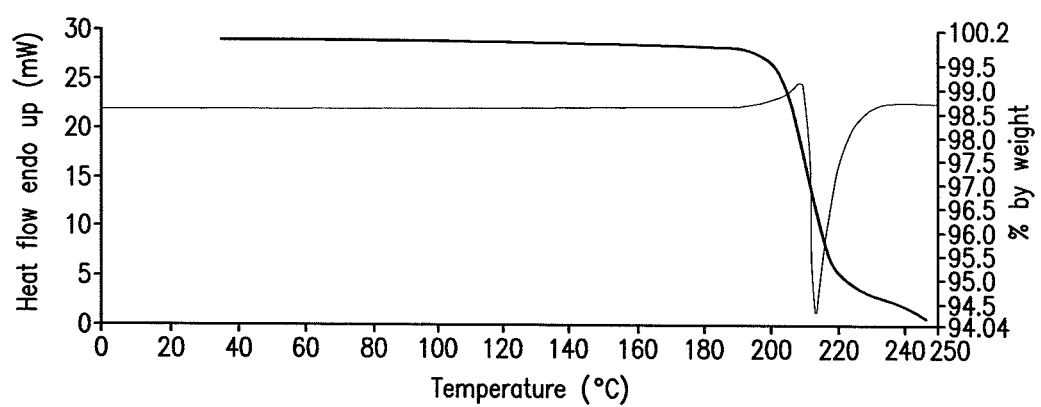
FIG. 10 shows the DSC and TGA thermograms of WX-671.1 (modification A).

In this example, thermograms were plotted by differential scanning calorimetry (DSC) and thermo-gravimetry (TGA). FIG. 10 shows the DSC and TGA thermograms of the WX-671.1 (modification A) stirred in isopropanol at 25° C. for one week. It decomposes from about 180° C. (exothermic peak in the DSC thermogram, mass loss in the TGA thermogram in the corresponding temperature range). The decomposition temperatures are strongly heating rate-dependent and were determined in the DSC calorimeter at a heating rate of 2 Kmin$^{-1}$. The DSC table measurements shown were recorded at a heating rate of 2 Kmin$^{-1}$. The decomposition is correspondingly recorded at higher temperatures.

At 150° C., no significant mass loss is recorded. The weakly pronounced endothermic effect before the decomposition peak could be caused by partial melting or partial conversion.

Figure 11:
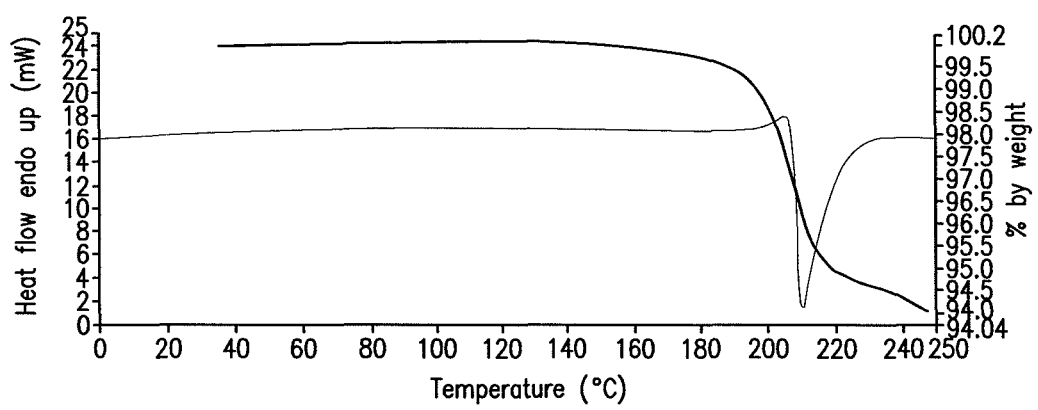
FIG. 11 shows the DSC and TGA thermograms of a sample (mesophase B) of WX-671.1.

FIG. 11 shows the DSC thermogram of a sample of WX-671.1 (mesophase B) employed for this screening. Modification A and mesophase B are thermoanalytically identical. Mesophase A was obtained from isopropanol (room temperature/refrigerator) and ethanol (room temperature).

Figure 12:
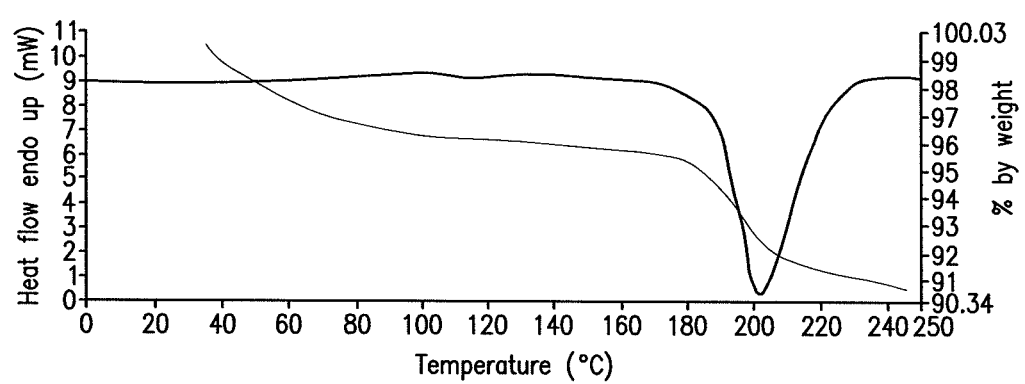
FIG. 12 shows the DSC and TGA thermograms of mesophase C of WX-671.1.

FIG. 12 shows the DSC and TGA thermograms of the active compound after a crystallization attempt from methanol at room temperature (mesophase C). It decomposes from about 156° C. (heating rate 2 Kmin$^{-1}$). Up to 175° C., a mass loss of 4.5% is recorded. In the DSC thermogram, the endothermic effect before the decomposition peak is missing. This form is present in a less ordered state than modification A and mesophase B. It is formed after crystallization attempts from methanol (room temperature, refrigerator) and ethanol (refrigerator). Mass losses of between 4.5 and 4.8% by weight were recorded in the samples. The stoichiometric value for the mass loss of 2 molecules of water per active compound molecule is 4.7%. This form, however, is not a hydrate.

Example 6

Thermomicroscopy of WX-671.1 (Hydrogensulfate Salt)

Thermomicroscopic recordings of a sample of WX-671.1 were made (not shown). Agglomerates were observed which show no specific habit. The active compound decomposes with bubble formation from about 197° C. Differences to the decomposition temperature observed in the DSC calorimeter come about due to the different heating rates. WX-671.1 is obtained in nonspecific form from solvents. The active compound shows double diffraction in some cases, as is characteristic of crystalline and mesomorphic substances.

Example 7

X-ray Diffractometry of WX-671.1 (Hydrogensulfate Salt)

Figure 13:
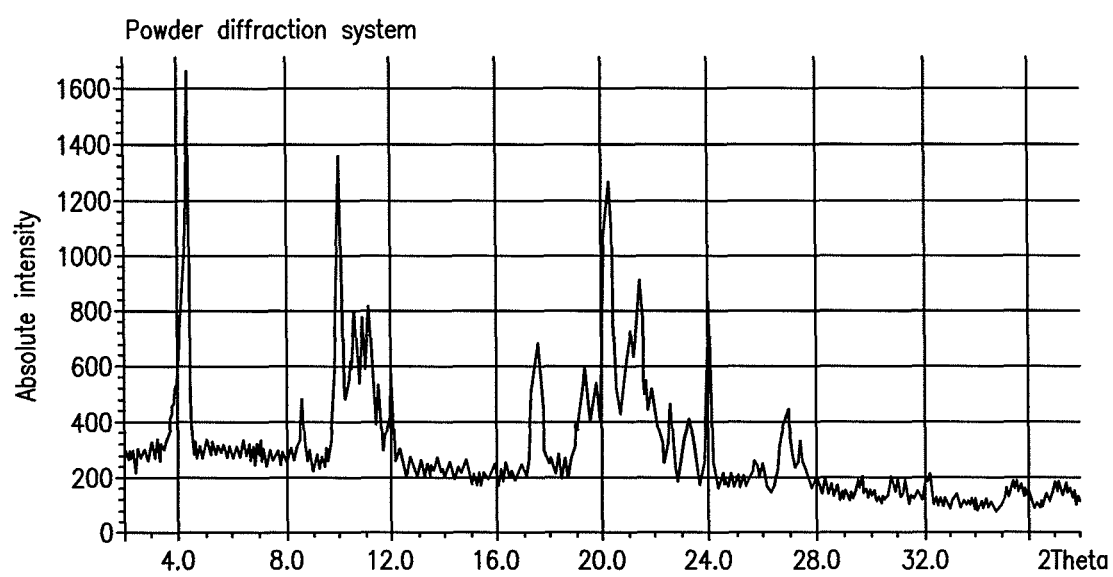
FIG. 13 shows the X-ray diffractogram of modification A of WX-671.1.

The X-ray diffractogram of modification A (FIG. 13) shows the pattern of numerous sharp peaks at higher 2-theta angles characteristic of crystalline phases. For the confirmation of the existence of a crystalline phase, further investigations, e.g. an X-ray structural analysis, are carried out.

Figure 14:
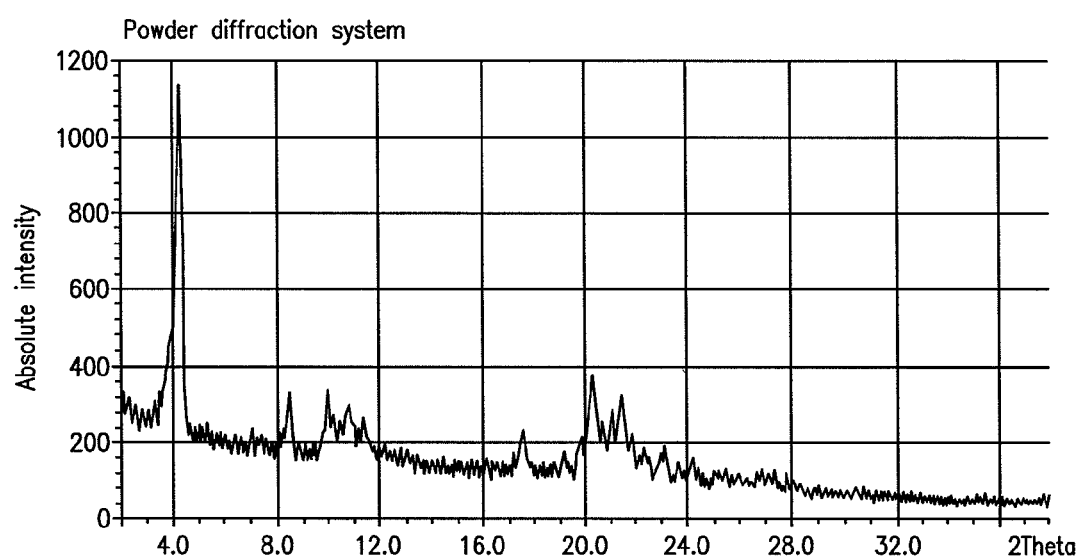
FIG. 14 shows the X-ray diffractogram of mesophase B of WX-671.1.

In the X-ray diffractogram of mesophase B (FIG. 14), a sharp peak was observed at a 2-theta angle of about 5° and further reflections of low intensity between about 8° and about 25°. The position and number of the peaks is similar to those of modification A. The peak present at low theta angle indicates the presence of a remote arrangement of the molecules; the peaks of low intensity verify the presence of a close arrangement. It can be concluded from this that mesophase B is present neither in crystalline nor in amorphous form, but presumably as a mesophase.

Figure 15:
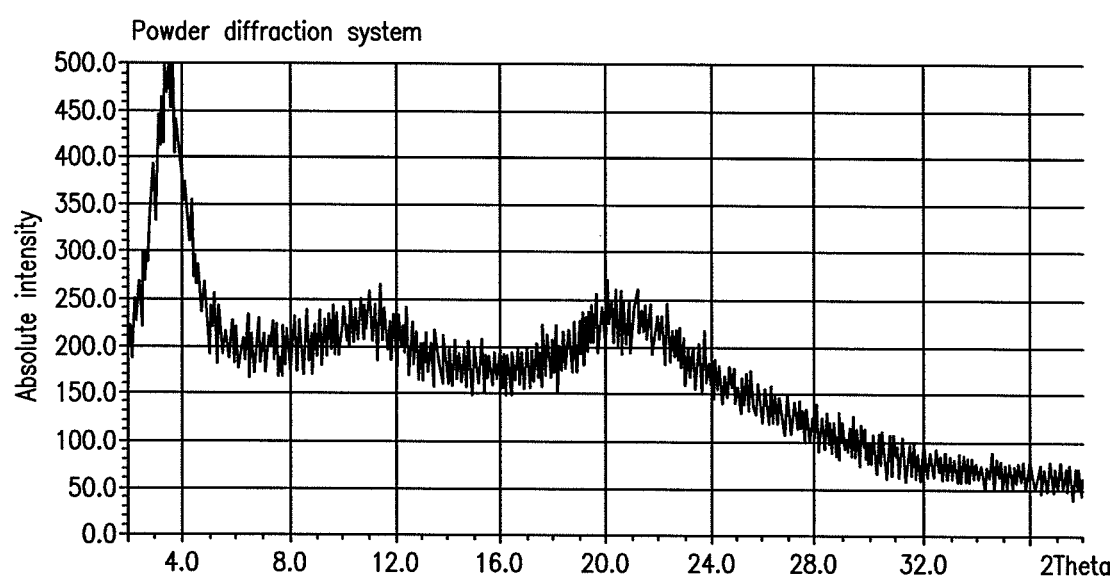
FIG. 15 shows the X-ray diffractogram of mesophase C of WX-671.1.

The X-ray diffractogram of mesophase C (FIG. 15) likewise shows a pattern characteristic of mesomorphic compounds: an intensive peak at low 2-theta angle. The X-ray diffractogram verifies that mesophase C is not a crystalline phase and because of the remote arrangement present cannot be considered part of the amorphous phase. Comparison with the X-ray diffractogram of mesophase B shows that mesophase C presumably forms a phase having a low degree of organization. An indication of this is the strongly pronounced and more intensive reflections in mesophase B between the 2-theta angles of about 8° and about 25°.

By stirring in isopropanol at room temperature for one week, mesophase B changes into modification A. It does not change due to stirring in water:ethanol (1:1). It likewise does not alter due to mechanical stress (grinding in a mortar, compressing at 9 kbar).

TABLE 7.1

X-ray diffractometry peak list for crystalline
modification of WX-671.1 (hydrogensulfate salt)
WX 671.1
Reflections
2 theta

| |
|---|
| 4.3 |
| 8.6 |
| 10.1 |
| 10.3 |
| 10.6 |
| 11.0 |
| 11.2 |
| 11.3 |
| 11.6 |
| 12.0 |
| 12.3 |
| 13.8 |
| 14.8 |
| 15.9 |
| 17.5 |
| 17.7 |
| 19.3 |
| 19.7 |
| 20.2 |
| 21.0 |
| 21.4 |
| 21.7 |
| 21.9 |
| 22.6 |
| 23.3 |
| 24.0 |
| 25.8 |
| 26.9 |
| 27.4 |
| 28.0 |
| 29.7 |
| 30.8 |
| 31.3 |
| 32.2 |
| 33.3 |
| 35.5 |
| 37.1 |

Example 8

Recrystallizations of WX-671 (Free Base)

The active compound WX-671 is investigated for polymorphism thermoanalytically (DSC, TGA), by X-ray diffractometry and by crystallizations from organic solvents. WX-671 crystallizes in one modification (modification A). The active compound shows a very low tendency for crystallization.

Modification A is the thermodynamically stable form at room temperature. A final assessment of the polymorphism and pseudopolymorphism of WX-671 is only possible after carrying out a polymorphism study.

WX-671 was dissolved in solvents (tetrahydrofuran, acetonitrile, methanol) of different polarity. The solutions were filtered, divided into four and the active compound was crystallized at different rates. After drying at room temperature, the thermograms (DSC, TGA) and the X-ray diffractograms were recorded.

The starting substance employed for the polymorphism screening could be prepared in mainly crystalline form.

The crystallization was possible from acetonitrile in the freezer at about −18° C.

Example 9

Differential Scanning Calorimetry (DSC) and Thermo-Gravimetry (TGA) of WX-671 (Free Base)

Figure 16:
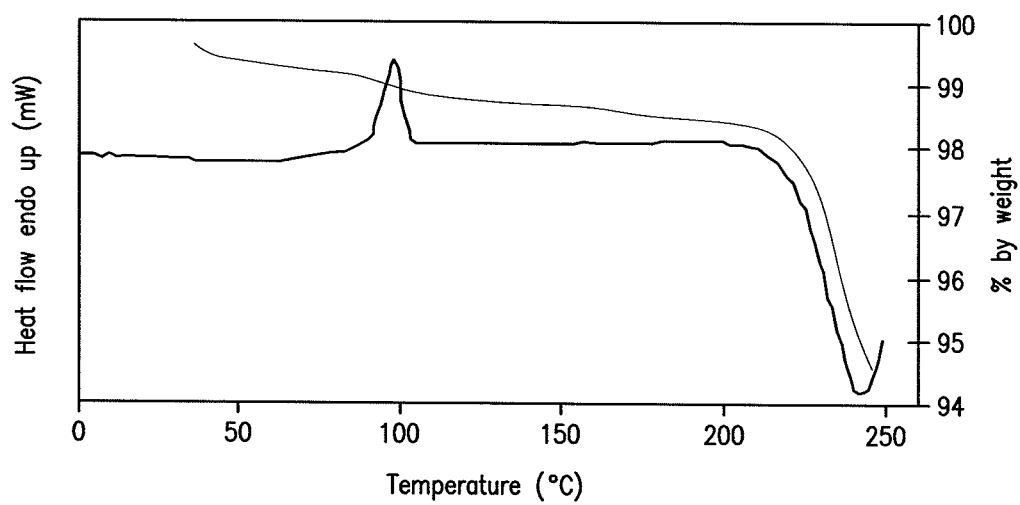
FIG. 16 shows the DSC and TGA thermograms of the amorphous starting substance of the free base WX-671.
Figure 17:
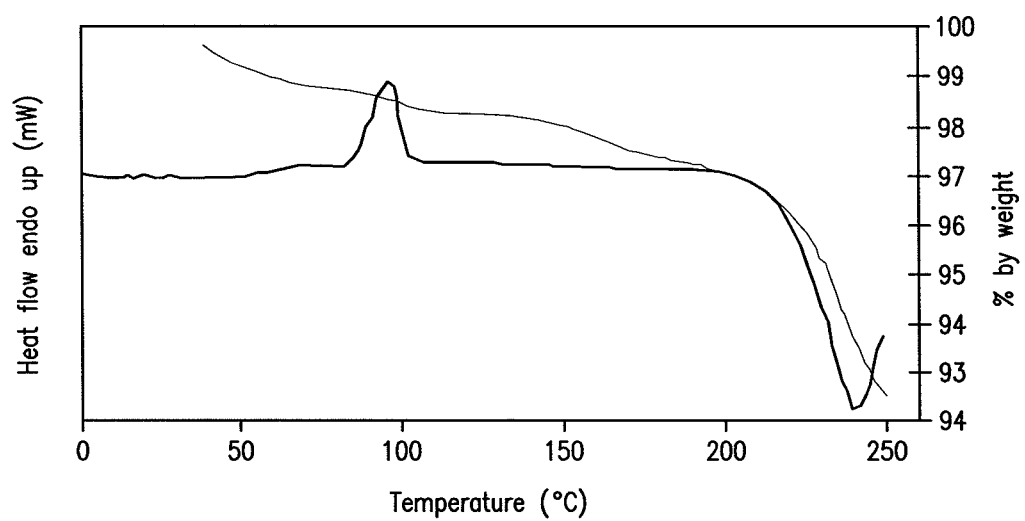
FIG. 17 shows the DSC and TGA thermograms of a sample of the free base WX-671 crystallized from acetonitrile in the freezer.

FIG. 16 shows the DSC and TGA thermograms of the amorphous starting substance. Just like the DSC/TGA thermograms of the greatest part of the other samples investigated, it shows a thermal effect in the range between 45° C. and 85° C. It was not possible to assign this thermal effect in the course of the polymorphism screening. It could be a glass transition. Conclusions as to a crystal form having a melting point of about 190° C. could follow from this. Depending on the heating rate, the substance decomposes from about 155° C. For this reason, the melting point of the crystalline sample (GBA 190903-8c) cannot be determined. The thermograms of the amorphous and crystalline substance are therefore largely identical (FIGS. 16 and 17).

Example 10

Microscopy of WX-671 (Free Base)

Figure 18:
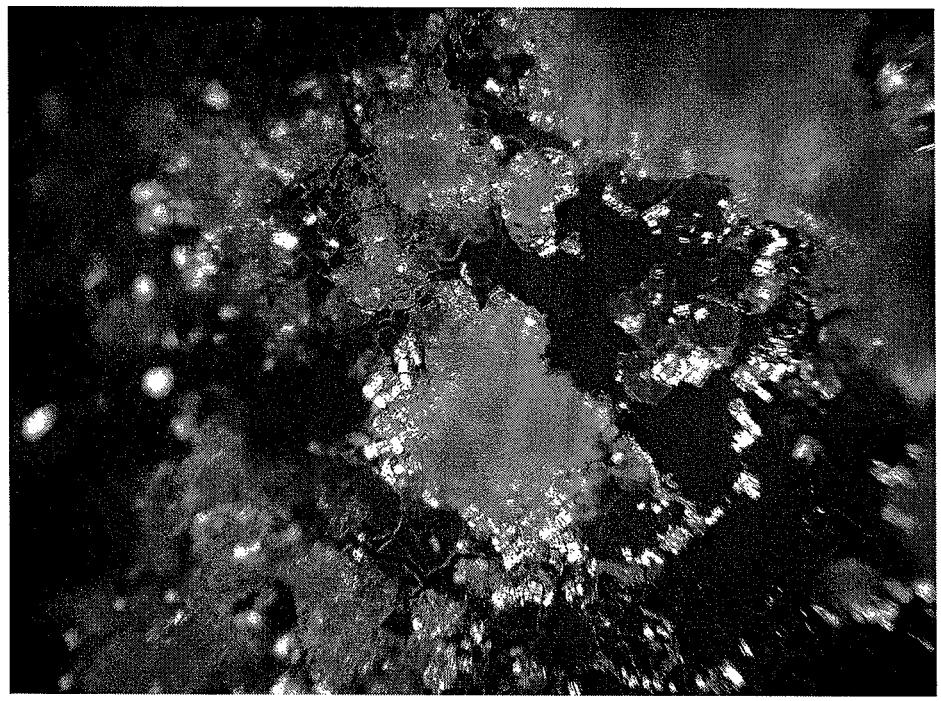
FIG. 18 shows a micrograph of the free base WX-671 after crystallization from acetonitrile in the freezer.

WX-671 crystallizes from acetonitrile in the freezer in the form of prisms (FIG. 18). The active compound does not crystallize or only crystallizes to a very small amount from other solvents; it does not crystallize from the melt.

Example 11

X-ray Diffractometry of WX-671 (Free Base)

Figure 19:
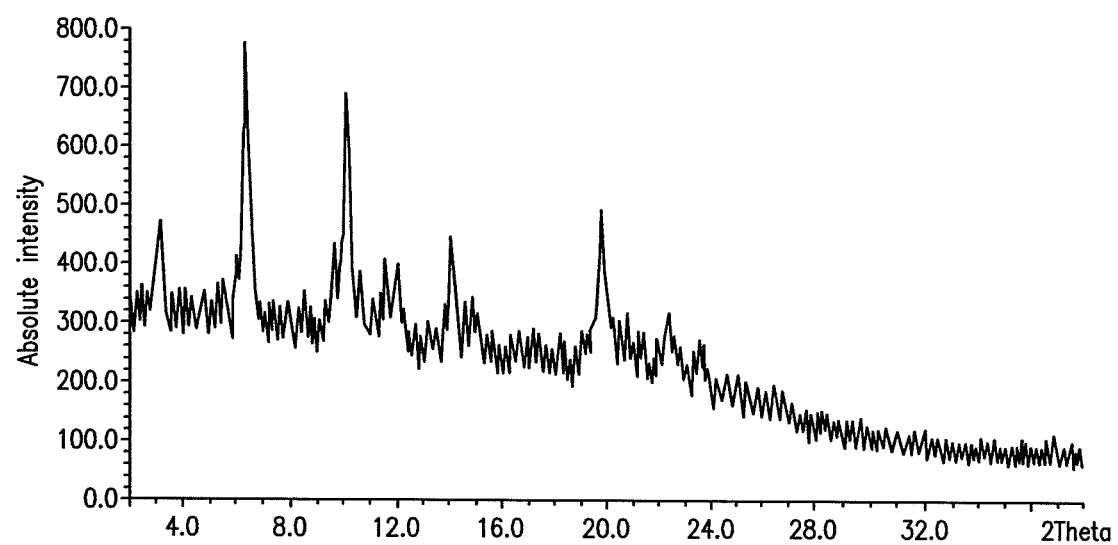
FIG. 19 shows the X-ray diffractogram of the free base WX-671 after crystallization from acetonitrile in the freezer.

FIG. 19 shows the X-ray diffractogram of the active compound after crystallization from acetonitrile in the freezer (modification A).

TABLE 11.1

X-ray diffractometry peak list for WX-671 (free base)
The sample was crystallized from acetonitrile in the
freezer.
WX 671
Reflections
2 theta

| |
|---|
| 3.2 |
| 5.5 |
| 6.4 |
| 8.5 |
| 9.7 |
| 10.2 |
| 10.7 |
| 11.2 |
| 11.5 |

TABLE 11.1-continued

X-ray diffractometry peak list for WX-671 (free base)
The sample was crystallized from acetonitrile in the freezer.

WX 671
Reflections
2 theta 11.7
12.1
13.4
13.8
14.1
14.6
14.8
15.5
16.5
18.1
19.1
19.7
20.5
20.7
21.3
22.4
22.7
23.6
26.5

Example 12

Moist Sorption of WX-671 (Free Base)

Figure 20:
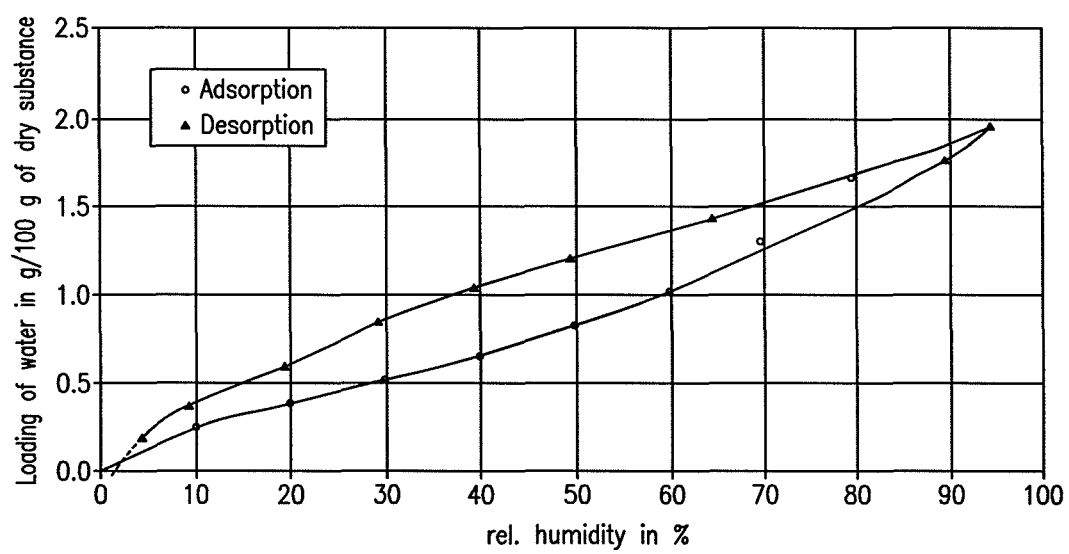
FIG. 20 shows the sorption isotherm of water vapor on the free base WX-671 at 22° C.

FIG. 20 shows the sorption isotherm of water vapor on WX-671 at 22° C. The amorphous active compound takes up water continuously from 0% r.h. to 95% r.h. On drying, this water is given off again. At most points of the isotherm, no equilibrium state was achieved within the respective stopping time. The sample weight increased or fell further. There was no indication of hydrate formation in this experiment.

Example 13

Stability of WX-671 (Free Base)

By stirring in diisopropyl ether and ethanol/water (1:1) at room temperature for one week, the active compound does not crystallize or crystallizes to a very small amount in modification A. It is not converted to any other polymorphic form. It is likewise not converted by mechanical stress (grinding in a mortar, compressing at 9 kbar); the crystallinity only decreases further.

The invention claimed is:

1. A method for the control of diseases which are associated with a pathological over expression of urokinase and/or the urokinase receptor in a patient in need of such control comprising administering to the patient an effective amount of a crystalline modification of N-α-(2,4,6-triisopropylphenylsulfonyl-)3-hydroxyamidino-(L)-phenyla-lanine 4-ethoxycarbonylpiperazide and/or salt thereof.

2. The method as claimed in claim 1 for tumor treatment and/or inhibition.

3. The method as claimed in claim 2 for the treatment and/or inhibition of formation of metastases.

4. The method as claimed in claim 2 for the treatment of primary tumors.

5. The method as claimed in claim 1, wherein the patient is administered an orally administrable composition in the form of tablets, coated tablets, capsules, pellets, powder, suppositories, solutions, syrup, emulsions, liposomes or/and suspension.

6. The method as claimed in claim 2 for tumor treatment.

7. The method as claimed in claim 3 for treatment for formation of metastases.

8. A method for the control of tumor and/or metastases in a patient in need of such control comprising:
administering to the patient an effective amount of a crystalline modification of N-α-(2,4,6-triisoprophylphenylsulfonyl-)3-hydroxyamidino-(L)-phenyla-lanine 4-ethoxycarbonylpiperazide and/or salt thereof.

9. The method as claimed in claim 1 for the treatment of pancreatic cancer or breast cancer.

* * * * *

UNITED STATES PATENT AND TRADEMARK OFFICE
CERTIFICATE OF CORRECTION

PATENT NO. : 8,492,385 B2  Page 1 of 1
APPLICATION NO. : 12/749140
DATED : July 23, 2013
INVENTOR(S) : Alfons Grunenberg et al.

It is certified that error appears in the above-identified patent and that said Letters Patent is hereby corrected as shown below:

In the Claims

In Claim 1, column 14, lines 17-19: please replace "N-α-(2,4,6-triisopropylphenylsulfonyl-)3-hydroxyamidino-(L)-phenyla- lanine 4-ethoxycarbonylpiperazide" with -- N- α -(2,4,6-triisopropylphenylsulfonyl-)3-hydroxyamidino-(L)-phenylalanine 4-ethoxycarbonylpiperazide --

In Claim 8, column 14, lines 35-37: please replace "N-α-(2,4,6-triisopropylphenylsulfonyl-)3-hydroxyamidino-(L)-phenyla- lanine 4-ethoxycarbonylpiperazide" with -- N- α -(2,4,6-triisopropylphenylsulfonyl-)3-hydroxyamidino-(L)-phenylalanine 4-ethoxycarbonylpiperazide --

Signed and Sealed this
Fifteenth Day of October, 2013

Teresa Stanek Rea
*Deputy Director of the United States Patent and Trademark Office*